United States Patent [19]

Shiota et al.

[11] Patent Number: 5,496,853
[45] Date of Patent: Mar. 5, 1996

[54] BENZOXA CONDENSED RING COMPOUNDS, PROCESS FOR PRODUCING THE SAME AND PHARMACEUTICAL COMPOSITION COMPRISING THE SAME

[75] Inventors: Tatsuki Shiota; Takumi Takeyasu, both of Hino; Kenichiro Kataoka, Tokyo; Tsutomu Mochizuki, Hino; Hirofumi Tanabe, Hino; Mikio Ota, Hino; Masatoshi Kano, Hino; Hisao Yamaguchi, Hino, all of Japan

[73] Assignee: Teijin Limited, Osaka, Japan

[21] Appl. No.: 429,023

[22] Filed: Apr. 26, 1995

Related U.S. Application Data

[63] Continuation of Ser. No. 78,274, filed as PCT/JP91/01793, Dec. 27, 1991, abandoned.

[30] Foreign Application Priority Data

Dec. 28, 1990 [JP] Japan ..................... 2-415443
Jan. 31, 1991 [JP] Japan ..................... 3-029143

[51] Int. Cl.$^6$ .............. C07D 301/79; C07D 263/56; A61K 31/34; A61K 31/42
[52] U.S. Cl. .............. 514/469; 514/253; 514/320; 514/337; 514/340; 514/375; 544/368; 544/376; 546/197; 546/264; 546/270; 548/217; 548/224; 549/407; 549/467
[58] Field of Search ..................... 549/467; 514/469

[56] References Cited

U.S. PATENT DOCUMENTS

| | | |
|---|---|---|
| 3,634,462 | 11/1972 | Lynch et al. . |
| 4,018,735 | 4/1977 | Nakagawa et al. ........ 548/224 |
| 4,296,240 | 10/1981 | Damon . |
| 4,297,349 | 10/1981 | Barcza . |
| 4,400,294 | 8/1983 | Martini et al. ........ 548/224 |
| 4,649,149 | 3/1987 | Gallay et al. ........ 514/375 |
| 4,780,469 | 10/1988 | Toda et al. ........ 514/382 |
| 4,847,257 | 7/1989 | Hupe et al. ........ 514/269 |
| 4,939,141 | 7/1990 | Toda et al. ........ 514/230.5 |
| 4,981,864 | 1/1991 | Von Der Saal et al. ........ 514/375 |
| 5,057,526 | 10/1991 | Von Der Saal et al. ........ 514/375 |
| 5,214,206 | 5/1993 | Picard et al. ........ 549/467 |
| 5,246,927 | 9/1993 | Rao ........ 514/375 |
| 5,376,681 | 12/1994 | Aono et al. ........ 549/467 |

FOREIGN PATENT DOCUMENTS

| | | |
|---|---|---|
| 57-18670 | 1/1982 | Japan . |
| 61-171462 | 8/1986 | Japan . |
| 61-280460 | 12/1986 | Japan . |
| 2169283 | 7/1986 | United Kingdom . |
| 92-12144 | 7/1992 | WIPO ............... 548/224 |

OTHER PUBLICATIONS

English–language Abstracts for JP–A–61–171462 and JP–A–61–280460 (1986).

*Primary Examiner*—Donald G. Daus
*Attorney, Agent, or Firm*—Sughrue, Mion, Zinn, Macpeak & Seas

[57] ABSTRACT

Pharmaceutical compositions containing a benzoxazole compound and a 2,3-dihydrobenzofuran compound represented by the following formula (I) and its pharmaceutically acceptable salt:

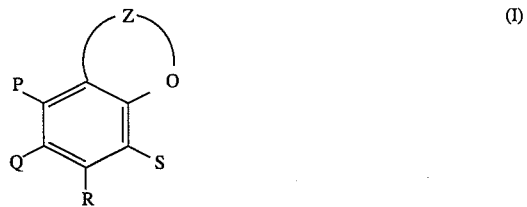

(I)

In the formula, any one of P, Q, R and S is a group represented by the formula:

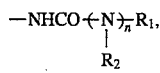

and $R_1$, $R_2$ and the reining three substituents out of the substituents P to S each independently stand for various substituents. These compositions are used as an ATCAT inhibitor or for treating hyperlipidemia and atherosclerosis.

8 Claims, No Drawings

BENZOXA CONDENSED RING COMPOUNDS, PROCESS FOR PRODUCING THE SAME AND PHARMACEUTICAL COMPOSITION COMPRISING THE SAME

This is a continuation of application Ser. No. 08/078,274 filed as PCT/JP91/01793, Dec. 27, 1991 abandoned.

TECHNICAL FIELD

The present invention relates to a pharmaceutical composition containing a benzoxa condensed ring compound, and more specifically, it relates to a pharmaceutical composition containing a benzoxazole or 2,3-dihydrobenzofuran compound, which is useful for inhibiting the action of Acyl-Coenzyme A: Cholesterol Acyltransferase (i.e., "ACAT" herein below). Furthermore, the present invention relates to a process for producing the above-mentioned compound and a novel compound belonging to the category of the above-mentioned compound.

BACKGROUND ART

As is well known in the art, atherosclerosis is a very important factor causative of various cardiovascular diseases, and extensive and intensive studies have been conducted with a view to suppression of the progress of atherosclerosis or regression of atherosclerosis. In particular, the efficacy of a drug for lowering cholesterol in the serum or arterial wall is recognized. However, an ideal drug having a significant clinical effect and less liable to occurrence of an adverse effect has not been realized in the art.

In recent years, it has become apparent that the accumulation of a cholesterol ester in an arterial wall is an important factor causative of the progress of atherosclerosis. Therefore, a lowering in the cholesterol level in the blood is useful for suppression of the progress of atherosclerosis and regression of the atherosclerosis.

Cholesterol in foods is esterified in tunica mucosa intestini tenuis and then incorporated as chylomicron in the blood. It is known that ACAT plays an important role in the formation of a cholesterol ester in the tunica mucosa intestini tenuis or arterial wall. Therefore, it is considered that the inhibition of ACAT in the tunica mucosa intestini tenuis and the prevention of the esterification can prevent the absorption of the cholesterol, and the cholesterol level of the blood can be lowered.

In the arterial wall, the cholesterol is accumulated as a cholesterol ester. Therefore, it is expected that the inhibition of ACAT in the arterial wall can effectively prevent the accumulation of the cholesterol ester.

Thus, an ACAT inhibitor is considered likely to become a drug useful for treating hyperlipidemia and atherosclerosis through the prevention of the cholesterol in intestinum tenue and the accumulation of the cholesterol in the arterial wall.

For example, urea derivatives (see, for example, J. Med. Chem., vol. 29, 1131 (1986) and Japanese Unexamined Patent Publication (Kokai) Nos. 63-316761 (which corresponds to EP-A-293880 and 1-93569 (which corresponds to EP-A- 297610)) and amide derivatives (see, for example, Japanese Examined Patent Publication (Kokoku) No. 63-54718 (which corresponds to U.S. Pat. No. 4,296,240 and U.S. Pat. No. 4,297,349) and Japanese Unexamined Patent Publication (Kokai) No. 63- 253060 (which corresponds to U.S. Pat. No. 4,716,175) have hitherto been reported as the above-mentioned ACAT enzyme inhibitor. In all the above-mentioned compounds, although the aromatic nucleus is bonded to a nitrogen atom of a urea or amide portion directly or through an alkylene group, no compound is disclosed wherein a benzoxazole condensed ring, that is, benzoxazole or 2,3-dihydrobenzofuran ring, is directly bonded to a nitrogen atom of the urea or amide portion.

It is known that some compounds wherein benzoxazole or 2,3-dihydrobenzofuran ring is directly bonded to a nitrogen atom of a urea or amide portion can be used as an intermediate for synthesizing drugs, insecticides, vermifuges, bacteriocides for agriculture and gardening, herbicides, photographic materials, etc. However, it is unknown whether or not they have an ACAT inhibitory activity. Examples of the former compound known in the art include compounds for use as an insecticide, wherein a substituted arylcarbonyl group is bonded to one of the nitrogen atoms of a ureylene group bonded to the benzene ring (see Japanese Unexamined Patent Publication (Kokai) No. 64-42474); compounds for use as a vermifuge, wherein a substituted or unsubstituted phenylamide group

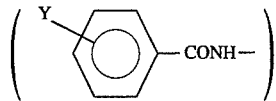

is bonded to the benzene ring (see Canadian Patent No. 842258); calcimycin (A-23187) known as Ca ionophore and derivatives thereof (see J. Am. Chem. Soc., 104, 1436 (1982); and Japanese Unexamined Patent Publication (Kokai) No. 62-26283 (which corresponds to Derwent Abstract 87-74940)) and several derivatives for use as an optomagnetic material and a heat-resistant material (see Journal of The Society of Organic Synthetic Chemistry, vol. 29, p. 717; and Japanese Examined Patent Publication (Kokoku) No. 64-53303 (which corresponds to U.S. Pat. No. 4,400,294)). Examples of the latter compound known in the art include compounds for use as a herbicide, wherein a chloroacetamide group is bonded to the benzene ring (see Japanese Patent Unexamined Patent Publication (Kokai) No. 60-109585 (which corresponds to Derwent Abstract 85-181198)); compounds for use as a bacteriocide for agriculture and gardening, wherein a substituted phenylamide group is bonded to the benzene ring (see Japanese Unexamined Patent Publication (Kokai) No. 60-215680 (which corresponds to Derwent Abstract 85-307995)); compounds for use as a starting compound for a pigment, wherein an acetylacetamide group is bonded to the benzene ring (see Japanese Examined Patent Publication (Kokoku) No. 47-7715 (which corresponds to U.S. Pat. No. 3,634,462)); compounds for use as a herbicide, wherein a substituted aryloxyisopropylamide group is bonded to the benzene ring (see Japanese Unexamined PCT Patent Publication (Kohyo) No. 61-501991 (which corresponds to WO-A- 86-2642 and EP-A-199794)); compounds for use as an antiallergic drug, wherein a tetrazole group is located as an indispensable group at the 2-position and a substituted phenylamide group is bonded to the benzene ring (see Japanese Unexamined Patent Publication (Kokai) No. 2-138242 (which corresponds to U.S. Pat. No. 4,780,469, U.S. Pat. No. 4,847,257 and U.S. Pat. No. 4,939,141)); compounds for use as an analgesic, wherein an acetamide group is bonded to the benzene ring (see Spanish Patent No. 512355); compounds for use as a herbicide, wherein a methyl or cyclopropyl group is bonded to one nitrogen atom of a ureylene group bonded to the benzene ring (see Canadian Patent No. 117860); and compounds for use as a photosensitive material for silver halide color photography, wherein a substituted alkylamide group or a substituted phenylamide group is bonded to the benzene ring (see Japanese Unexamined Patent Publication (Kokai) Nos. 61-250642 (which corresponds to Derwent Abstract 86-335324) and 61-233742 (which corresponds to Derwent Abstract 86-315479)). The above-described prior art documents are, however, silent on the fact that benzoxazole or 2,3-dihydrobenzofuran derivatives, including the above-described known compounds, have an ACAT inhibitory activity.

DISCLOSURE OF THE INVENTION

Accordingly, an object of the present invention is to provide a pharmaceutical composition having an ACAT enzyme inhibitory activity and capable of exhibiting an excellent therapeutic effect through a lowering in the level of cholesterol in the blood or arterial wall, a novel derivative containing a benzoxa condensed ring capable of exhibiting a significant effect and a process for producing the same.

The present inventors have made extensive and intensive studies with a view to providing compounds significantly superior to known anti-hyperlipidemic agents and anti-atheroscleotic agents and, as a result, have unexpectedly found that certain amides or urea derivatives having a benzoxazole or 2,3-dihydrobenzofuran ring have not only a strong ACAT inhibitory activity but also strong anti-hyperlipidemic activity and anti-atheroscleotic activity, which has led to the completion of the present invention.

In accordance with the present invention, the above-mentioned object of the present invention can be attained by providing a pharmaceutical composition comprising a benzoxa condensed ring compound represented by the following formula (I) or its pharmaceutically acceptable salt in an amount effective for inhibiting the action of Acyl-coenzyme A: Cholesterol Acyltransferase:

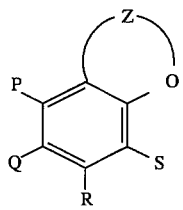

(I)

wherein any one of P, Q, R and S is a group represented by the formula:

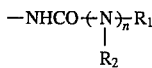

with the remaining three substituents being independently a group represented by the formula —$R_3$, wherein $R_1$ stands for a group selected from the group consisting of:

(i) an unsubstituted cycloalkyl or cycloalkenyl group or a cycloalkyl or cycloalkenyl group substituted at a position other than the 1-position with the substituent being a $C_1$–$C_{14}$ alkyl, alkoxy, acylamino, monoalkylamino, alkyloxycarbonyl, acyl or acyloxy group or a $C_2$–$C_{26}$ dialkylamino group;

(ii) a group represented by the formula:

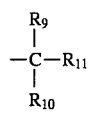

wherein $R_9$ and $R_{10}$ each independently stands for a hydrogen atom or a lower alkyl group, or may combine with each other to form a $C_3$–$C_7$ carbon ring; and $R_{11}$ stands for a substituted or unsubstituted $C_1$–$C_{19}$ alkyl, $C_2$–$C_{19}$ alkenyl, $C_6$–$C_{10}$ aryl, $C_7$–$C_{19}$ arylalkyl or $C_1$–$C_{19}$ acyl group or acyl group having a $C_4$–$C_{19}$ aromatic ring, provided that the substituent when said groups are substituted is a halogen atom, an amino, nitro, cyano, carboxyl or hydroxyl group, a $C_1$–$C_{16}$ alkyl, alkoxy, acylamino, monoalkylamino, alkyloxycarbonyl, acyl or acyloxy group, or a $C_2$–$C_{26}$ dialkylamino group; or $R_{11}$ stands for a group represented by the formula:

wherein A stands for a $C_1$–$C_{12}$ alkylene chain;

X stands for an oxygen atom, a sulfur atom, or a group represented by the formula:

wherein $R_{12}$ stands for a hydrogen atom or a lower alkyl or acyl group or may combine with B to form a cyclic amine, provided that, when a cyclic amine is formed, an oxygen atom, a sulfur atom, a nitrogen atom or a nitrogen atom substituted with a lower alkyl or arylalkyl group may be contained as a constituent member of the ring; and B stands for a substituted or unsubstituted alkyl, aryl or arylalkyl group, provided that the substituent when said groups are substituted is a halogen atom, an amino, nitro, cyano, carboxyl or hydroxyl group, a $C_1$–$C_{12}$ alkyl, alkoxy, monoalkylamino, acylamino, alkyloxycarbonyl, acyl or acyloxy group, or a $C_2$–$C_{20}$ dialkylamino group; and (iii) a substituted or unsubstituted aryl group or a group represented by the formula:

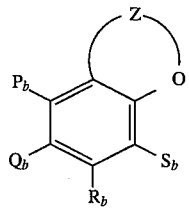

wherein any one of $P_b$, $Q_b$, $R_b$ and $S_b$ represents a bond with the remaining three substituents independently standing for a group represented by the formula —$R_3$, provided that, when the aryl group is substituted, the substituent is present at the o-, m- or p-position and a halogen atom, an amino, nitro, cyano, carboxyl or hydroxyl group, a $C_1$–$C_{16}$ alkyl, alkoxy, monoalkylamino, acylamino, alkyloxycarbonyl, acyl or acyloxy group, or a $C_2$–$C_{26}$ dialkylamino group; and the alkyl portion of said groups may be interrupted by:

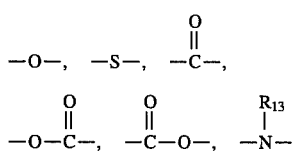

wherein $R_{13}$ stands for a hydrogen atom or a lower alkyl, acyl or arylalkyl group, arylene or arylenoxy, or 1 to 3 hydrogen atoms on the carbon atom may be substituted with an aryl or aryloxy group, a halogen atom or a cyano group, or the aryl portion as the substituent may be substituted with a halogen atom, an amino, nitro, cyano, carboxyl or hydroxyl group, or a lower alkyl, alkoxy, monoalkylamino, dialkylamino, acylamino, alkyloxycarbonyl, acyl or acyloxy group;

$R_2$ stands for a hydrogen atom or a $C_1$–$C_8$ alkyl group;

each $R_3$ independently stands for a hydrogen atom, a halogen atom, an amino, nitro, cyano, carboxyl or hydroxyl group, $C_1$–$C_{20}$ alkyl, alkoxy, acylamino, monoalkylamino, alkyloxycarbonyl, acyl or acyloxy group, or a $C_2$–$C_{26}$ dialkylamino group; and the alkyl portion of said groups may be interrupted by:

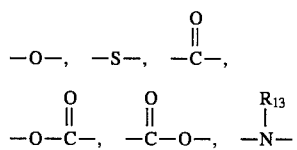

wherein $R_{13}$ stands for a hydrogen atom or a lower alkyl, acyl or arylalkyl group, arylene or arylenoxy, or 1 to 3 hydrogen atoms on the carbon atom may be substituted with an aryl or aryloxy group, a halogen atom or a cyano group, or the aryl portion as the substituent may be substituted with a halogen atom, an amino, nitro, cyano, carboxyl or hydroxyl group, a $C_1$–$C_{20}$ alkyl, alkoxy, monoalkylamino, acylamino, alkyloxycarbonyl, acyl or acyloxy group, or a $C_2$–$C_{26}$ dialkylamino group; and Z stands for a linking group which combines with an O atom, a carbon atom of the benzene ring, to which the O atom is bonded, and a carbon atom adjacent to said carbon atom to form a five-membered ring and is represented by the formula:

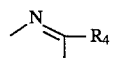

or

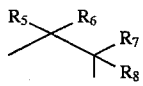

wherein $R_4$ stands for a hydrogen atom, a $C_1$–$C_{20}$ alkyl, alkenyl or alkynyl group, or a substituted or unsubstituted aryl group, provided that the substituent when the aryl group is substituted is a halogen atom, an amino, nitro, cyano, carboxyl or hydroxyl group, a $C_1$–$C_{20}$ alkyl, alkoxy, monoalkylamino, acylamino, alkyloxycarbonyl, acyl or acyloxy group, or a $C_2$–$C_{26}$ dialkylamino group; and $R_5$, $R_6$, $R_7$ and $R_8$ each independently stand for a hydrogen atom or a $C_1$–$C_{20}$ alkyl group, or $R_5$ and $R_6$ or $R_7$ and $R_8$ combine with a carbon atom bonded thereto to form a $C_5$–$C_7$ carbon ring; and n is 0 or 1.

Further, the present invention provides a novel benzoxa condensed ring compound represented by the following formula ($I_a$) or its pharmaceutically acceptable salt which constitutes a preferred embodiment of the above-described pharmaceutical composition:

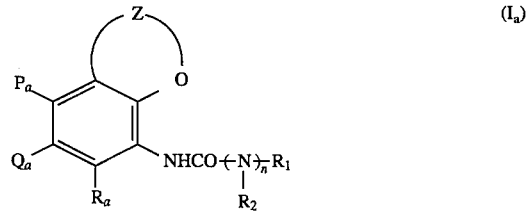

(I$_a$)

wherein $P_a$, $Q_a$ and $R_a$ each independently stand for a hydrogen atom, a halogen atom, or an amino, nitro, cyano, carboxyl or hydroxyl group, a $C_1$–$C_{20}$ alkyl, alkoxy, acylamino, monoalkylamino, alkyloxycarbonyl, acyl or acyloxy group, or a $C_2$–$C_{26}$ dialkylamino group; and the alkyl portion of said groups may be interrupted by:

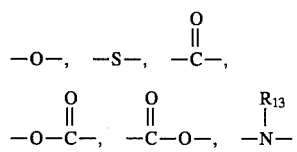

wherein $R_{13}$ stands for a hydrogen atom or a lower alkyl, acyl or arylalkyl group, arylene or arylenoxy, or 1 to 3 hydrogen atoms on the carbon atom may be substituted with an aryl or aryloxy group, a halogen atom or a cyano group, and the aryl portion as the substituent may be substituted with a halogen atom, an amino, nitro, cyano, carboxyl or hydroxyl group, a $C_1$–$C_{20}$ alkyl, alkoxy, monoalkylamino, acylamino, alkyloxycarbonyl, acyl or acyloxy group, or a $C_2$–$C_{26}$ dialkylamino group, provided that $R_a$ stands for a group other than the hydrogen atom among the groups described above in connection with the definition of Ra; and $R_1$, $R_2$, Z and n are as defined above.

Further, the present invention provides the following processes for producing compounds represented by the formula (I), that is, (A) a process for producing a compound represented by the formula (I) wherein n is 1, and its pharmaceutically acceptable salt, comprising reacting an isocyanate represented by the following formula (II):

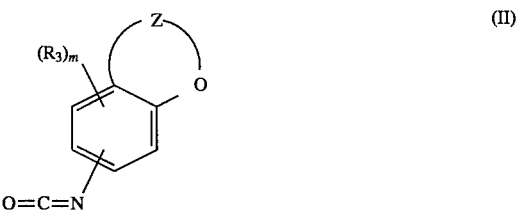

(II)

wherein m is an integer of 0 to 3; and $R_3$ and Z are as defined above, with an isocyanate represented by the following formula (III):

(III)

wherein $R_1$ and $R_2$ are as defined above, and optionally converting the reaction product to a salt;

(B) a process for producing a compound represented by the formula (I) wherein n is 1, and its pharmaceutically acceptable salt, comprising reacting an amine represented by the following formula (IV):

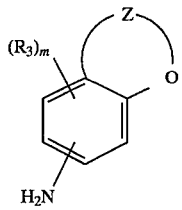
(IV)

wherein m, $R_3$ and Z are as defined above, with an isocyanate represented by the following formula (V):

$$O=C=N-R_1 \quad (V)$$

wherein $R_1$ is as defined above, and optionally converting the reaction product to a salt; and (C) a process for producing a compound represented by the above-mentioned formula (I) wherein n is 0, and its pharmaceutically acceptable salt, comprising reacting an amine represented by the formula (IV) with a carboxylic acid represented by the following formula (VI) or its reactive derivative:

$$R_1COOH \quad (VI)$$

wherein $R_1$ is as defined above, and optionally converting the reaction product to a salt.

Other objects and advantage of the present invention will be apparent from the following description.

BEST MODE FOR CARRYING OUT THE INVENTION

In accordance with to the present invention, there is provided a pharmaceutical composition comprising a compound, which partially includes a known compound, for use in the treatment of diseases developed by the action of ACAT, which compounds are unknown to have an ACAT inhibitory activity and to be useful for treating the diseases. In the present invention, the term "treatment" is used in such a concept that the compound represented by the formula (I) is used for any of therapeutic and preventive purposes.

Furthermore, in accordance with the present invention, there is provided a novel compound which can be used particularly advantageously for the treatment of the above-mentioned diseases.

In the description in connection with the compounds and derivatives in the present specification, the term "lower" is used in such meaning that, in groups to which the term is affixed, for example, alkyl, alkenyl, alkynyl, alkoxy, acylamino, mono- or di-alkylamino, acyl and acyloxy groups and the alkyl, alkenyl or alkynyl portion of arylalkyl groups may take any of chain (straight-chain or branched) and cyclic forms having a 1 to 6 carbon atoms, unless otherwise specified. Accordingly, specific examples of the lower alkyl group include methyl, ethyl, propyl, isopropyl, butyl, isobutyl, sec-butyl, tert-butyl, pentyl, neopentyl, hexyl, cyclopropyl, cyclohexyl and cyclopropylmethyl.

Also when the above-described groups have a larger number of carbon atoms, they are used in such meaning that they may take any of chain (straight-chain or branched) and cyclic forms, unless otherwise specified.

The expression "the alkyl portion is interrupted by:

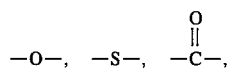

or the like" is intended to mean that a suitable carbon-carbon bond of the alkyl chain may take a bonding form, such as carbon-O-carbon.

In the compounds of the formula (I) used for attaining the object of the present invention, Z in the formula combines with an oxygen atom bonded to the benzene ring, a carbon atom of the benzene ring, to which the oxygen atom is bonded, and a carbon atom adjacent to said carbon atom to form a five-membered ring, and the compounds of the formula (I) are roughly classified into groups of compounds, that is, benzoxazole derivatives (i.e., Z being a linking group represented by the formula:

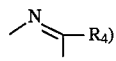

and 2,3-dihydrobenzofuran derivatives (i.e., Z being a linking group represented by the formula:

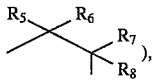

and further classified into amide derivatives wherein each n is 0, and urea derivatives wherein n is 1.

More specifically, the benzoxa condensed ring compounds belonging to the first group of compounds according to the present invention are benzoxazole derivatives represented by the following formula (I-1):

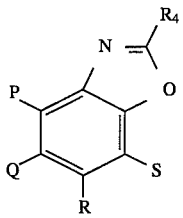
(I-1)

wherein P, Q, R, S and $R_4$ are as defined above, and the second group of compounds are 2,3-dihydrobenzofuran derivatives represented by the following formula (I-2):

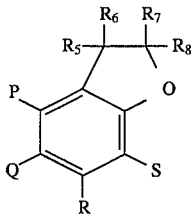
(I-2)

wherein P, Q, R, S, $R_5$, $R_6$, $R_7$ and $R_8$ are as defined above.

In the formulae (I-1) and (I-2), the groups Q to S are of equal significance from the viewpoint of the object of the present invention, and any one of these groups stands for a group represented by the formula:

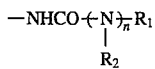

with the remaining substituents each independently standing for a group $R_3$. Therefore, the group represented by the above-described formula may be bonded to any of the 4- to 7-positions (P, Q, R, S) in the benzene ring of the compounds represented by the formulae (I-1) and (I-2). However, compounds wherein the group represented by the above-mentioned formula is bonded to the 7-position (S) is particularly preferred from the viewpoint of the intended drug efficacy and are important also because most of them are novel compounds.

In the formulae (I-1) and (I-2), the $R_1$ stands for (i) an unsubstituted cycloalkyl or cycloalkenyl group, or a cycloalkyl or cycloalkenyl group substituted at its position other than the 1-position; a group represented by the formula:

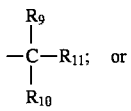

a substituted or unsubstituted aryl group or a group represented by the formula:

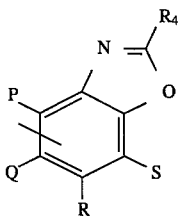

or

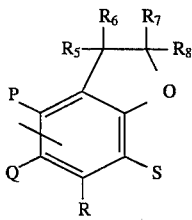

wherein the bonding group substitutes for the group:

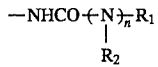

with the remaining groups being as defined above.

In the $R_1$, favorable specific examples of the unsubstituted cycloalkyl or cycloalkenyl group or cycloalkyl or cycloalkenyl group substituted at its position other than the 1-position include cyclopentyl, cyclohexyl, cycloheptyl, 1-cyclohexen-1-yl, 4-hexylcyclohexyl and 4-decyloxycyclohexyl.

When the $R_1$ stands for a group represented by the formula:

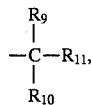

the $R_9$ and $R_{10}$ each independently stand for a hydrogen atom or a lower alkyl group, or combine with each other to form a $C_3$–$C_7$ carbon ring.

Examples of the lower alkyl group include those described above, and when the $R_9$ and $R_{10}$ combine with each other to form a $C_3$–$C_7$ carbon ring, examples of the $R_1$ include a group represented by the following formula:

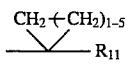

In the $R_{11}$, favorable examples of the substituted or unsubstituted $C_1$–$C_{19}$ alkyl include, besides the above-described lower alkyls, isohexyl, octyl, decyl, undecyl, dodecyl, tridecyl, pentadecyl, hexadecyl, heptadecyl, nonadecyl, icosyl, 1,1-dimethylheptyl, 1,1-dimethylundecyl, 1,1,12,12-tetramethyltridecyl, 1-methyltridecyl, 1-decylcyclohexyl, 1-decylcyclopentyl, 1-dodecylcyclopropyl, 1-cyclohexyl-1-methylethyl, 1-ethyloctyl and 10,10-dimethylundecyl.

In the $R_{11}$, examples of the $C_2$–$C_{19}$ alkenyl include vinyl, allyl, butenyl, hexenyl, 8-tridecenyl, 8-heptadecenyl, 9-octadecenyl, 8,11-heptadecanedienyl, 1,1-dimethyl-8-nonenyl, cyclohexenylmethyl, 2-cyclopenten-1-yl, 2,4-cyclopentadien-1-yl, 3-cyclohexen-1-yl and 2,5-cyclohexadien-1-yl.

Specific examples of the $R_{11}$ when the $R_{11}$ stands for a $C_6$–$C_{10}$ aryl group include phenyl, naphthyl, pyridyl and thienyl. Accordingly, in this case, specific examples of the $R_1$ include benzyl, 1-phenylcyclopentyl, 1-phenylethyl and 1-methyl-1-(2-pyridyl)ethyl. Favorable specific examples of the $R_1$ when the $R_{11}$ stands for a $C_7$–$C_{19}$ aryl alkyl include 2-phenylethyl, 8-phenyloctyl, 1,1-dimethyl-11-phenylundecyl, 1-benzylcyclopentyl, (1-phenylcyclopentyl)methyl, 1,1-dimethyl-4-(1-methyl-1,2,3,4-tetrahydroquinolin-6-yl)butyl, 1,1-dimethyl-7-pyridylheptyl, 2,2-diphenylethyl, 1,1-dimethyl-6-phenylhexyl, 1,1-dimethyl-7-phenylheptyl, 1,1-dimethyl-5-phenylpentyl and 1,1-dimethyl-4-phenylbutyl.

Favorable examples of the $R_{11}$ when the $R_{11}$ stands for a $C_1$–$C_{19}$ chain acyl group, $C_4$–$C_{19}$ cyclic hydrocarbon acyl group or a acyl group having a aromatic ring include groups wherein a carbonyl group is bonded to a favorable group of the above-described alkyl, cyclic alkyl, chain alkenyl, cyclic alkenyl, aryl and arylalkyl groups.

The $R_{11}$ embraces also groups wherein one or more hydrogen atoms, preferably 1 to 3 hydrogen atoms, on carbon(s) in the chain or on carbons constituting the ring are substituted with halogen atoms (for example, fluorine, chlorine, bromine and iodine, preferably fluorine and chlorine), amino, nitro, cyano, carboxyl and hydroxyl groups and further $C_1$–$C_{16}$ alkyl (as described above), alkoxy (for example, lower alkoxy, such as methoxy, ethoxy and propoxy, pentadecanoxy, decyloxy and octyloxy), acylamino (for example, lower acylamino, such as acetamide, propionylamino, butyrylamino and heptanoylamino, and lauroylamino and palmitoylamino), mono-or di-alkylamino (for example, methylamino, ethylamino, dimethylamino, diethylamino and decanylamino), alkyloxycarbonyl (for example, groups wherein a carbonyl group is bonded to the above-described alkoxy, such as methoxycarbonyl and ethoxycarbonyl), acyl (formyl, acetyl, propionyl, isovaleryl, pivaloyl, myristoyl, palmitoyl, etc.), and acyloxy (acetyloxy, pivaloyloxy, myristoyloxy, etc.). Specific examples of the $R_1$ having $R_{11}$ substituted with the above-described groups include 1,1-dimethyl-11-chloroundecyl, 1,1-dimethyl-7-bromoheptyl, 9-ethoxycarbonylnonyl, 1,1-dimethyl-11-hydroxyundecyl, 1,1-dimethyl-10-carboxyldecyl, 1-(4-dimethylaminophenyl)cyclopentyl, 1-methyl-1-(4-chlorophenyl)ethyl, 1-methyl-1-(4-octyloxyphenyl)ethyl, [1-(4-chloro)phenylcyclopentyl], [1-(4-dimethylamino)phenylcyclopentyl] methyl, 1,1-dimethyl-4-(4-isobutyl)phenylbutyl, 1,1-dimethyl-4-(4-hexyloxy)phenylbutyl, 1,1-dimethyl-2-(4-decyloxy)phenylethyl, 1,1-dimethyl-2-(4-decylamino)phenylethyl and 1,1-dimethyl-7-(4-chloro)phenylheptyl groups.

Alternatively, the $R_{11}$ may stand for a group represented by the formula —A—X—B wherein A stands for a $C_1$–$C_{12}$ alkylene chain; X stands for an oxygen atom, a sulfur atom, or a group represented by the formula:

$$\begin{array}{c} R_{12} \\ | \\ -N- \end{array}$$

wherein $R_{12}$ stands for a hydrogen atom or a lower alkyl or acyl group or may combine with B to form a cyclic amine, provided that, when a cyclic amine is formed, an oxygen atom, a sulfur atom, a nitrogen atom or a nitrogen atom substituted with a lower alkyl or arylalkyl group may be contained as a constituent member of the ring; and B stands for a substituted or unsubstituted alkyl, aryl or arylalkyl group. The alkylene in the A is a divalent group formed by further eliminating one hydrogen atom from the alkyl group, and examples thereof include those corresponding to the alkyl groups specifically described above. Examples of the lower alkyl and acyl groups in the $R_{12}$ include the same groups as those described above in connection with the lower alkyl group and acyl group. Favorable specific examples of the cyclic amine when $R_{12}$ combines with B to form a cyclic amine include 1-pyrrolidinyl, piperidino, morpholino, thiomorpholino, 4-methyl- 1-piperazinyl and 4-benzyl-1-piperazinyl. The alkyl group and arylalkyl group in the B have the same meaning as the alkyl group and arylalkyl group defined above, and preferred examples thereof are also the same as those of the alkyl group and arylalkyl group described above.

Also when the $R_{11}$ stands for a group represented by the formula —A—X—B, each group may be substituted in the same manner as that described above in connection with each group of $R_{11}$. Favolable specific examples of the $R_1$ having $R_{11}$ substituted with the above-described groups include 6-isobutoxyhexyl, 6-p-chlorophenoxyhexyl, 5-p-dimethylaminophenoxypentyl, 5-isohexyloxy-1,1-dimethylpentyl, 7-isohexyloxy-1,1-dimethylheptyl, 7-isobutoxy- 1,1-dimethylheptyl, 7-neopentyloxy-1,1-dimethylheptyl, 5-p-chlorophenoxy-1,1-dimethylpentyl, 6-p-chlorophenoxy-1,1-dimethylhexyl, 7-p -chlorophenoxy-1,1-dimethylheptyl, 1,1-dimethyl-7-p-tolyloxyheptyl, 5-(p-tert-butylphenoxy-pentyl, 1,1-dimethyl-6-p-dimethylaminophenoxyhexyl, 1,1-dimethyl-7-p-dimethylaminophenoxyheptyl, 7-isopropylamino-1,1-dimethylheptyl, 7-benzylamino-1,1-dimethylheptyl, 7-(N-benzyl-N-methylamino)- 1,1-dimethylheptyl, 7-(N-p-chlorobenzyl-N-methylamino)- 1,1-dimethylheptyl, 7-(N-p-chlorophenyl-N-methylamino)- 1,1-dimethylheptyl, 1,1-dimethyl- 7-piperidinoheptyl, 1,1-dimethyl-7-(4-methyl-1-piperazinyl)heptyl, 7-(4-benzyl-1-piperazinyl)-1,1-dimethylheptyl, 5-(4-benzyl-1-piperazinyl)-1,1-dimethylpentyl, 6-(p-chlorophenylthio)-1, 1-dimethylhexyl, 1,1-dimethyl-6-p-nitrophenoxyhexyl, 1,1-dimethyl-6-p-fluorophenoxyhexyl, 1,1-dimethyl-6-p-aminophenoxyhexyl, 1,1-dimethyl-6-(2,4-dichloro)phenoxyhexyl, 1,1-dimethyl- 7-p-fluorophenoxyheptyl, 1,1-dimethyl-6-p-hexyloxyphenyloxyhexyl, 1,1-dimethyl-7-morpholinoheptyl and 1,1-dimethyl-6-cyclohexylethylhexyl.

When the $R_1$ stands for a substituted or unsubstituted aryl group, the aryl group has the same meaning as the aryl group defined above in connection with the $R_{11}$, except that the aryl group is bonded to the carbon atom of the carbonyl group or the nitrogen atom of the group represented by the formula $$\begin{array}{c} R_2 \\ | \\ -N- \end{array}$$

of an amide or urea portion of the formula (I-1) or (I-2). The substituted aryl group has a suitable substituent at the o-, m- or p-position relative to the site of bonding to the amide or urea (ureylene) portion. Preferred specific examples of these substituents include the same groups as those described above in connection with the $R_{11}$. When these substituents have a particularly long chain alkyl portion, the alkyl portion may be interrupted by:

$$-O-, \quad -S-, \quad \overset{O}{\underset{\|}{-C-}},$$

$$\overset{O}{\underset{\|}{-O-C-}}, \quad \overset{O}{\underset{\|}{-C-O-}}, \quad \overset{R_{13}}{\underset{|}{-N-}}$$

(wherein $R_{13}$ stands for a hydrogen atom or a lower alkyl or acyl group), arylene or arylenoxy. The term "arylene" used herein is intended to mean a divalent group formed by eliminating one hydrogen atom from an aryl group, and specific examples thereof include those formed by eliminating one hydrogen atom from the aryl group specifically described above. The alkyl portion and aryl (or arylene) portion of these substituents as well may be substituted with one or more substituents, preferably 1 to 3 substituents, as described above connection with the $R_{11}$. Among them, particularly preferred examples include p-fluorophenyl, p-decylphenyl, p-methoxyphenyl, p-isohexyloxyphenyl, p-decyloxyphenyl, p-butyrylaminophenyl, p-(N-butyl-N-methylamino, phenyl, p-valeryloxyphenyl, m-heptanoylphenyl, 4-[6-(4-chlorophenyloxy)hexyloxy] phenyl, 4-decylaminophenyl, 4-decanamidephenyl, m-decyloxyphenyl, 4-[6-(4-dimethylaminophenyloxy)-hexyloxy] phenyl, 3-chloro -4-decyloxyphenyl, 4-[6-(N-methyl-N-benzylamino)hexyloxy] phenyl and 3-dimethylamino-4-decyloxyphenyl groups.

Further examples of the $R_1$ include a group represented by the formula:

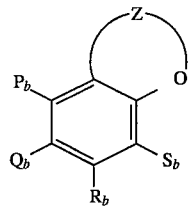

wherein $P_b$ to $S_b$ and Z have the same meaning the corresponding $P_a$ to $S_b$ and Z described above, except that one of the $P_b$ to $S_b$ stands for a linking group instead of the group represented by the formula:

$$-NHCO+N\frac{}{n}R_1.$$
$$\phantom{-NHCO+N}|$$
$$\phantom{-NHCO+N}R_2$$

When the $R_1$ has the above-described group, examples of the compound represented by the formula (I) include compounds comprising combination of the following moieties.

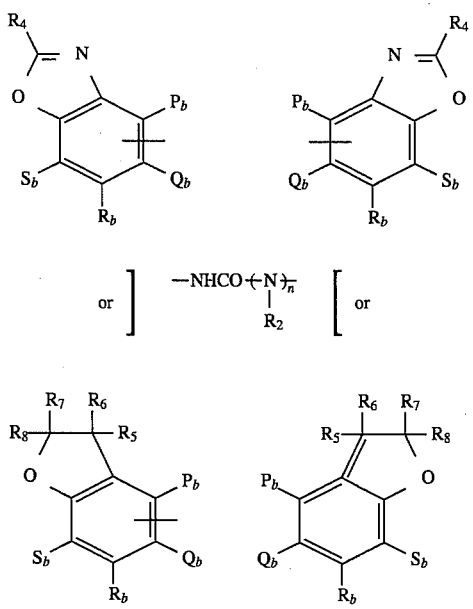

Therefore, the compound represented by the formula (I) include also a compound having such a structure that the above-described individual moieties are linked together through the divalent linking group of the ureylene group or amide group indicated at the center of the above-described structural formulae and the linking group of the left and right condensed ring moieties.

The $R_2$ stands for a hydrogen atom or a $C_1$–$C_8$ alkyl group. Favorable examples of the alkyl group include, besides the above-described specific examples of the lower alkyl group, heptane, octane, cyclohexylmethyl and cyclohexylethyl.

When P, Q, R and S in the formulae (I-1) and (I-2) stand for a group other than the group represented by the formula:

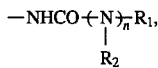

the remaining three groups each independently stand for a hydrogen atom, a halogen atom, an amino, nitro, cyano, carboxyl or hydroxyl group, a $C_1$–$C_{20}$ alkyl, alkoxy, acylamino, monoalkylamino, alkyloxycarbonyl, acyl or acyloxy group, or a $C_2$–$C_{26}$ dialkylamino group; and the alkyl portion of these groups may be interrupted by:

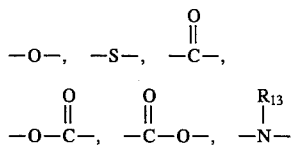

wherein $R_{13}$ stands for a hydrogen atom or a lower alkyl, acyl or arylalkyl group,
arylene or arylenoxy, or 1 to 3 hydrogen atoms on the carbon atom may be substituted with an aryl or aryloxy group, a halogen atom or a cyano group, or the aryl portion as the substituent may be substituted with a halogen atom, an amino, nitro, cyano, carboxyl or hydroxyl group, a $C_1$–$C_{20}$ alkyl, alkoxy, monoalkylamino, acylamino, alkyloxycarbonyl, acyl or acyloxy group, or a $C_2$–$C_{26}$ dialkylamino group.

The meaning and specific examples of these groups are the same as the meaning and specific examples of the corresponding groups described above in connection with the $R_1$. More preferably, when any three of the groups P, Q, R and S stand for a group other than the group represented by the formula:

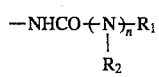

although these three groups may be the same or different, if the $R_1$ stands for a group having a large number of constituent atoms (number of carbon atoms: 10 to 20), these groups preferably comprise a group having a small number of constituent atoms, for example, a hydrogen atom, a halogen atom (particularly, fluorine, chlorine or bromine), an amino, nitro, cyano, carboxy or hydroxyl group, a lower alkyl group (particularly, methyl, ethyl, propyl or isopropyl), a lower alkyloxy group (particularly, methoxy, ethoxy or propoxy), a lower acylamino group (particularly, acetamide or propionylamide), a mono- or di-lower alkylamino group (particularly, methylamino, ethylamino or dimethylamino), a lower alkyloxycarbonyl group (particularly, methoxycarbonyl or ethoxycarbonyl), a lower acyl group (particularly, acetyl, propionyl or butyryl), or a lower acyloxy group (particularly, acetyloxy or propionyloxy). On the other hand, when the $R_1$ is a group having a small number of constituent atoms (number of carbon atoms: 6 or less), it is preferred that at least one group among the P, Q, R and S except for the group represented by the formula:

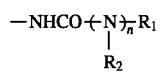

be a group having a large number of constituent atoms. Specific examples of the group having a large number of constituent atoms include decyloxy, decanoylamide, dodecyloxy, 4-decyloxybenzoylamide, decyl, decylamino, 2,2-dimethyldodecaneamido, 6-(4-chlorophenyl)hexyloxy, 4-(6-phenyloxy)hexyloxybenzoyl and 6-(N-methyl-N-4-chlorobenzyl)aminohexyloxy.

As described above, the compound represented by the formula (I) wherein a group represented by the formula:

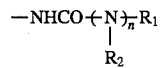

is bonded to the 7-position (S) is particularly preferred from the viewpoint of drug efficacy. In this case, it is still preferred for the 6-position (R) to be a group other than a hydrogen atom from the viewpoint of the drug efficacy. In particular, when the $R_1$ contained in the group bonded to the 7-position stands for a group having a large number of constituent atoms, it is preferred for the substituent at the 6-position to be a lower alkyl, a lower alkoxy or a halogen.

when the $R_4$ in the formula (I-1) stands for a $C_1$–$C_{20}$ alkyl group, specific examples of such an alkyl group are the same as those of the alkyl group described above in connection with the definition of P, Q, R and S. When the $R_4$ stands for an alkenyl group, the alkenyl group is preferably a lower alkenyl group and examples thereof include vinyl, propenyl and cyclohexenyl. When the $R_4$ stands for an alkyl group, the alkynyl group is preferably a lower alkynyl group and examples thereof include ethynyl and propynyl. When the $R_4$ stands for a substituted or unsubstituted aryl group, examples of the substituent are the same as those of the substituent at the site of the aryl in the definition of the $R_{11}$ and preferred examples thereof include a halogen atom, a lower alkyl, a lower alkoxy, a lower acyl, a lower alkylamino or a lower alkyloxycarbonyl. When the $R_4$ stands for the above-described aryl group, favorable specific examples of the aryl group include phenyl, pyridyl, thienyl, 4-methylphenyl, 4-chlorophenyl, 4-methoxyphenyl, 4-decanoxyphenyl and 3-nitrophenyl.

When the $R_5$, $R_6$, $R_7$ and $R_8$ in the formula (I-2) stand for a $C_1$–$C_{20}$ alkyl group, specific examples of such an alkyl group are the same as those of the alkyl group described in connection with the $R_4$. Among them, a lower alkyl, such as methyl, ethyl, propyl and isopropyl, are particularly preferred. These four groups may be the same or different. It is preferred that the $R_5$ and $R_6$ stand for a hydrogen atom with the $R_7$ and $R_8$ standing for a lower alkyl group. When $R_5$ and $R_6$ or $R_7$ and $R_8$ combine with a carbon atom bonded thereto to form a $C_5$–$C_7$ carbon ring, favorable specific examples of such a carbon ring include $C_5$–$C_7$ carbon rings described above in connection with the $R_{11}$.

Compounds represented by the formula (Ia), more specifically, benzoxazole compounds represented by the following formula (Ia-1):

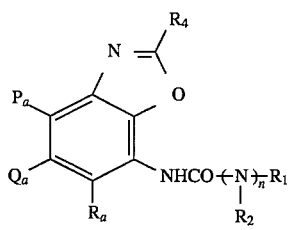

wherein $P_a$, $Q_a$, $R_a$, $R_1$, $R_2$, $R_4$ and n are as defined above, provided that $R_a$ stands for a group other than a hydrogen atom, and 2,3-dihydrobenzofuran compounds represented by the following formula (Ia-2):

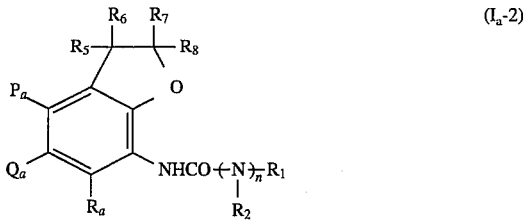

wherein $P_a$, $Q_a$, $R_a$, $R_1$, $R_2$, $R_5$, $R_6$, $R_7$, $R_8$ and n are as defined above, provided that $R_a$ stands for a group other than a hydrogen atom, are novel compounds not described in any conventional technical literature. Further, when the structural formula representing the compound of the present invention has an asymmetric carbon, the compound of the present invention includes all possible optical isomers.

Examples of compounds comprising specific combinations of groups will now be described for the purpose of more specifically describing the compounds and novel compounds used in the pharmaceutical composition of the present invention. In the following synoptical tables, code G is used according to need to represent the formula:

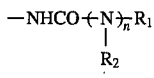

| Compound No. | R-S | $R_4$ | $R_1$ | $R_2$ | n |
|---|---|---|---|---|---|
| 101 | P,R = CH$_3$ Q = Cl, S = G | -(CH$_2$)$_8$CH$_3$ | cyclohexyl | H | 1 |
| 102 | R = OCH$_3$, S = G P,Q = H | -CH$_3$ | 4-methylphenyl-O-(CH$_2$)-CH$_3$ (phenyl with para-O-alkyl-CH$_3$ chain) | H | 1 |
| 103 | P = H Q,R = CH$_3$ S = G | 4-chlorophenyl | 4-methylphenyl-O-(CH$_2$)$_n$ with terminal 4-Cl-phenoxy | H | 1 |
| 104 | P = G, Q,R = CH$_3$ S = H | isobutyl | 4-methylphenyl | H | 1 |

| Compound No. | R-S | $R_4$ | $R_9$ | $R_{10}$ | $R_{11}$ | $R_2$ | n |
|---|---|---|---|---|---|---|---|
| 105 | S = G P,Q,R = H | phenyl | H | H | 1-phenylcyclopentyl | H | 1 |
| 106 | S = G P,Q,R = H | phenyl | H | H | -(CH$_2$)$_{10}$CH$_3$ | H | 1 |

-continued

| # | | | | | | |
|---|---|---|---|---|---|---|
| 107 | P = H Q,R = CH₃ S = G | phenyl | H | spirocyclopentane-phenyl | H | 1 |
| 108 | P = H Q,R = CH₃ S = G | phenyl | H | 4-(N,N-dimethylamino)-spirocyclopentane-phenyl | H | 1 |
| 109 | P = H Q,R = CH₃ S = G | phenyl | H | 4-chlorophenoxy-butyl | H | 1 |
| 110 | P,Q = H R = CH₃ S = G | —CH₃ | H | 4-chlorophenyl | —(CH₂)₅CH₃ | 1 |
| 111 | P,R = CH₃ Q = H S = G | 3-pyridyl | H | —(CH₂)₁₀CH₃ | H | 1 |
| 112 | P,Q = H R = O(CH₂)₉CH₃ S = G | —CH₃ | —CH₃ | —CH₃ | H | 1 |
| 113 | P,R = CH₃, Q = G S = H | —CH₃ | —CH₃ | spirocyclopentane-phenyl | H | 1 |
| 114 | Q = OCH₃, R = G P,S = H | —CH₂CH₃ | H | 4-chloro-N-methyl-benzyl-pentyl | H | 1 |

-continued

| Compound No. | R-S | R₄ | R₁ | n |
|---|---|---|---|---|
| 201 | R,Q = H R = O(CH₂)₉CH₃ S = G | —CH₃ | 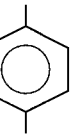 (cyclohexyl) | 0 |
| 202 | P = H Q,R = CH₃ S = G |  (4-chlorophenyl) |  (4-(nonyloxy)phenyl with OCH₂... CH₃) | 0 |
| 203 | P,R = CH₃ Q = O(CH₂)₃CH₃ S = G | isopropyl |  (4-chlorophenyl) | 0 |
| 204 | P,R = CH₃ Q = G S = H | —CH₃ |  (4-nonylphenyl) | 0 |
| 205 | P,R = CH₃ Q = OH S = G | —CH₃ |  (4-((4-chlorophenoxy)butoxy)phenyl) | 0 |

| Compound No. | P-S | R₄ | R₉* | R₁₀* | R₁₁ | n |
|---|---|---|---|---|---|---|
| 206 | S = G P,Q,R = H |  (pyridyl) | H | H | —(CH₂)₁₃CH₃ | 0 |
| 207 | S = G P,Q,R = H |  (pyridyl) |  (cyclopentyl) | | —(CH₂)₉CH₃ | 0 |
| 208 | S = G P,Q,R = H | —CH₃ | H | H | —(CH₂)₁₃CH₃ | 0 |

-continued

| Compound No. | P-S | R$_4$ | R$_9$ | R$_{10}$ | R$_{11}$ | n |
|---|---|---|---|---|---|---|
| 209 | S=G P,Q,R=H | —CH$_3$ |  | spiro-cyclopentane | —(CH$_2$)$_9$CH$_3$ | 0 |
| 210 | S=G P,Q,R=H | phenyl | H | H | —(CH$_2$)$_{13}$CH$_3$ | 0 |
| 211 | S=G P,Q,R=H | phenyl |  | spiro-cyclopentane | —(CH$_2$)$_9$CH$_3$ | 0 |
| 212 | P=H Q,R=CH$_3$ S=G | phenyl | CH$_3$ | CH$_3$ | 4-(pentyloxy)phenyl-C(CH$_3$)$_3$ | 0 |
| 213 | P=H Q,R=CH$_3$ S=G | phenyl |  | spiro-cyclopentane | —(CH$_2$)$_9$CH$_3$ | 0 |
| 214 | P=H Q,R=CH$_3$ S=G | —CH$_3$ | —CH$_3$ | —CH$_3$ | —(CH$_2$)$_9$CH$_3$ | n |
| 215 | P=H Q,R=CH$_3$ S=G | —CH$_3$ | —CH$_3$ | —CH$_3$ | 4-(isobutyl)phenyl-CH$_2$— | 0 |
| 216 | P=H Q,R=CH$_3$ S=G | —CH$_3$ | —CH$_3$ | —CH$_3$ | —(CH$_2$)$_5$—O—(4-Cl-C$_6$H$_4$) | 0 |
| 217 | P=H Q,R=CH$_3$ S=G | isopropyl | —CH$_3$ | —CH$_3$ | —(CH$_2$)$_5$—O—CH$_2$CH$_2$—O—CH$_3$ | 0 |
| 218 | P=H Q,R=CH$_3$ S=G | —(CH$_2$)$_8$CH$_3$ | —CH$_3$ | —CH$_3$ | —CH$_3$ | 0 |
| 219 | P=H Q,R=CH$_3$ S=G | 4-(—O—(CH$_2$)$_9$CH$_3$)phenyl | —CH$_3$ | —CH$_3$ | —CH$_3$ | 0 |

-continued

| | | | | |
|---|---|---|---|---|
| 220 | P = NO$_2$ Q,R = CH$_3$ S = G | —CH$_3$ | —CH$_3$ | —(CH$_2$)$_9$CH$_3$ | 0 |
| 221 | P = N(CH$_3$)$_2$ Q,R = CH$_3$ S = G | —CH$_3$ | —CH$_3$ | —(CH$_2$)$_9$CH$_3$ | 0 |
| 222 | P = H R = OCH$_3$ S = G | —CH$_3$ | —CH$_3$ |  | 0 |
| 223 | P,R = CH$_3$ Q = H S = G | —CH$_3$ | —CH$_3$ | 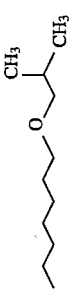 | 0 |
| 224 | P,R = CH$_3$ Q = Cl S = G | —CH$_3$ | —CH$_3$ | —(CH$_2$)$_9$CH$_3$ | 0 |
| 225 | P,R = CH$_3$ Q = N(CH$_3$)$_2$ S = G | —CH$_3$ | —CH$_3$ | —(CH$_2$)$_9$CH$_3$ | 0 |
| 226 | P,R = CH$_3$ Q = NH$_2$ S = G | —CH$_3$ | —CH$_3$ | —(CH$_2$)$_9$CH$_3$ | 0 |
| 227 | P,R = CH$_3$ Q = NHCOCH$_3$ S = G | —CH$_3$ | —CH$_3$ |  | 0 |
| 228 | P,R = H Q = CN S = G | 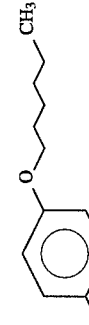 | —CH$_3$ |  | 0 |
| 229 | P = G Q,R = CH$_3$ S = H | —CH$_3$ |  |  | 0 |
| 230 | P,R = CH$_3$ Q = G S = H | —CH$_3$ | —CH$_3$ | —(CH$_2$)$_9$CH$_3$ | 0 |
| 231 | P,S = CH$_3$ Q = OCH$_3$ R = G |  | —CH$_3$ | —CH$_3$ | 0 |
| 232 | P,R = CH$_3$ Q = G S = H | —(CH$_2$)$_8$CH$_3$ | —CH$_3$ | —CH$_3$ | 0 |
| 233 | P,R = H Q = COCH$_3$ S = G |  | H | H | 0 |

-continued

| 234 | P,S = H Q = O(CH$_2$)$_9$CH$_3$ R = G | NO$_2$ | —CH$_3$ | —CH$_3$ | —CH$_3$ | 0 |

Structure showing phenyl ring with substituents P, Q, R, S and side chain with R$_4$, R$_5$, R$_7$, R$_8$, O.

| Compound No. | P–S | R$_5$–R$_8$ | R$_1$ | R$_2$ | n |
|---|---|---|---|---|---|
| 301 | P,Q = H R = O(CH$_2$)$_9$CH$_3$ S = G | R$_5$,R$_6$ = H<br>R$_7$,R$_8$ = CH$_3$ | cyclohexyl | H | 1 |
| 302 | P,R = CH$_3$ Q = NHCO(CH$_2$)$_8$CH$_3$<br>S = G | R$_5$,R$_6$ = H<br>R$_7$,R$_8$ = CH$_3$ | 4-chlorophenyl | H | 1 |
| 303 | P,R = CH$_3$ Q = G S = NH(CH$_2$)$_9$CH$_3$ | R$_5$,R$_6$ = H<br>R$_7$,R$_8$ = CH$_3$ | 4-methoxyphenyl | H | 1 |
| 304 | P = G R = H Q,S = CH$_3$ | R$_5$,R$_6$,R$_7$,R$_8$ = H | 4-(5-(4-chlorophenoxy)pentyloxy)phenyl | H | 1 |
| 305 | P,R = CH$_3$ Q = H S = G | R$_5$,R$_6$ = H<br>R$_7$,R$_8$ = CH$_3$ | 4-(nonyloxy)phenyl | H | 1 |

-continued
| Compound No. | P–S | R₅–R₈ | | |
|---|---|---|---|---|
| 306 | P,S = H Q = G R = CH₃ | R₅,R₆ = H<br>R₇,R₈ = CH₃ |  | H | 1 |
| 307 | P,Q = H R = CH₃ S = G | R₅,R₆ = H<br>R₇,R₈ = CH₃ |  | H | 1 |
| Compound No. | P–S | R₅–R₈ | R₉ | R₁₀ | R₁₁ | R₂ | n |
|---|---|---|---|---|---|---|---|
| 308 | P,Q = H R = CH₃ S = G | R₅,R₆ = H<br>R₇,R₈ = CH₃ | H | H | —(CH₂)₁₀CH₃ | H | 1 |
| 309 | P,Q = H R = CH₃ S = G | R₅,R₆ = H<br>R₇,R₈ = CH₃ | H | H | 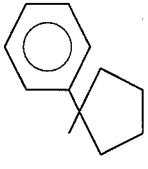 | H | 1 |
| 310 | P,S = H Q = G R = CH₃ | R₅,R₆ = H<br>R₇,R₈ = CH₃ | H | H | —(CH₂)₁₀CH₃ | H | 1 |
| 311 | P,S = H Q = G R = CH₃ | R₅,R₆ = H<br>R₇,R₈ = CH₃ | H | H | 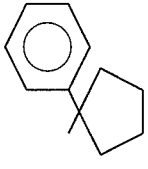 | H | 1 |

-continued

| Compound No. | P–S | R₅–R₈ | | R₁ | | n |
|---|---|---|---|---|---|---|
| 312 | P,R = CH₃  Q = H  S = G | R₅,R₆ = H<br>R₇,R₈ = CH₃ | H | 4-(pentyloxy)phenyl-spiro-cyclopentane | H | 1 |
| 313 | P,R = CH₃  Q = N(CH₃)₂<br>S = G | R₅,R₆ = H<br>R₇,R₈ = CH₃ | H | phenyl-spiro-cyclopentane | H | 1 |
| 314 | P,R = CH₃  Q = Cl  S = G | R₅,R₆ = H<br>R₇,R₈ = CH₃ | H | 4-chlorophenyl (ethyl) | cycloheptyl | 1 |
| 315 | P,R = CH₃  Q = H  S = G | R₅,R₆ = H<br>R₇,R₈ = CH₃ | H | 4-N(CH₃)₂-phenyl-spiro-cyclopentane | H | 1 |
| 316 | P,R = CH₃  Q = H  S = G | R₅,R₆,R₈ = H<br>R₇ = (CH₂)₉CH₃ | H | 4-chlorophenoxy | H | 1 |
| 317 | P,R = CH₃  Q = G  S = NHCOCH₃ | R₅,R₆ = H<br>R₇,R₈ = CH₃ | –CH₃ | 2-chloro-4-methylphenyl | H | 1 |
| 318 | R = H  Q,S = CH(CH₃)₂<br>R = G | R₅,R₆ = H<br>R₇,R₈ = CH₃ | –CH₃ | –CH₃ | H | 1 |
| 319 | P,R = CH₃  Q = G  S = N(CH₃)₂ | R₅,R₆ = H<br>R₇,R₈ = CH₃ | H | phenyl-spiro-cyclopentane | H | 1 |

| | | | |
|---|---|---|---|
| 401 | P,R = CH₃ Q = H S = G | R₅,R₆ = H R₇ = CH₃<br>R₈ = (CH₂)₈CH₃ | cyclohexyl | 0 |
| 402 | P,R = CH₃ Q = H S = G | R₅,R₆ = H R₇,R₈ = CH₃ | 4-heptylphenyl | 0 |
| 403 | P,R = CH₃ Q = H S = G | R₅,R₆ = H R₇,R₈ = CH₃ | 2-nitro-4-methyl-phenyl with O(CH₂)₇CH₃ | 0 |
| 404 | P,R = CH₃ Q = H S = G | R₅,R₆ = H R₇,R₈ = CH₃ | 2-(N(CH₃)₂)-4-methylphenyl with O(CH₂)₇CH₃ | 0 |
| 405 | P,R = CH₃ Q = H S = G | R₅,R₆ = H R₇,R₈ = CH₃ | 4-methylphenyl-O(CH₂)₇CH₃ | 0 |
| 406 | P,R = CH₃ Q = H S = G | R₅,R₆ = H R₇,R₈ = CH₃ | 4-methylphenyl-O(CH₂)₉CH₃ | 0 |
| 407 | P,R = CH₃ Q = H S = G | R₅,R₆ = H R₇,R₈ = CH₃ | 4-methylphenyl-O(CH₂)₁₁CH₃ | 0 |
| 408 | P,R = CH₃ Q = H S = G | R₅,R₆ = H R₇,R₈ = CH₃ | 4-methylphenyl-O-CH₂-(4-chlorophenyl) | 0 |

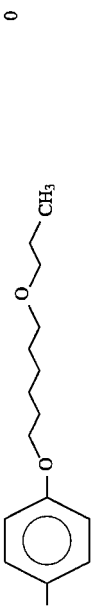

-continued

| Compound No. | P–S | $R_5$–$R_8$ | $R_9$ | $R_{10}$ | $R_{11}$ | n |
|---|---|---|---|---|---|---|
| 418 | P,R = CH$_3$ Q = N(CH$_3$)$_2$ S = G | $R_5,R_6$ = H $R_7,R_8$ = CH$_3$ | 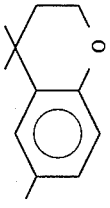 | | | 0 |
| 419 | P,R = CH$_3$ Q = NHCOCH$_3$ S = G | $R_5,R_6$ = H $R_7,R_8$ = CH$_3$ | 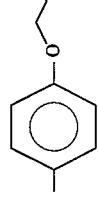 | | | 0 |
| 420 | P,R = CH$_3$ Q = NH(CH$_2$)$_9$CH$_3$ S = G | $R_5,R_6$ = H $R_7,R_8$ = CH$_3$ | 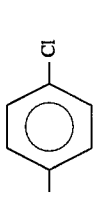 | | | 0 |
| 421 | P,R = CH$_3$ Q = NHCO(CH$_2$)$_{10}$CH$_3$ S = G | $R_5,R_6$ = H $R_7,R_8$ = CH$_3$ | 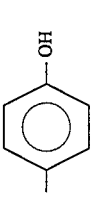 | | | 0 |
| 422 | P,R = CH$_3$ S = G Q = NHCOC(CH$_3$)$_2$(CH$_2$)$_9$CH$_3$ | $R_5,R_6$ = H $R_7,R_8$ = CH$_3$ | 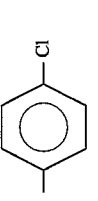 | | | 0 |
| 423 | P,R = CH$_3$ Q = G S = NHCOC(CH$_3$)$_3$ | $R_5,R_6$ = H $R_7,R_8$ = CH$_3$ | 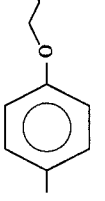 | | | 0 |
| 424 | P,R = CH$_3$ Q = OH S = G | $R_5,R_6$ = H $R_7,R_8$ = CH$_3$ | 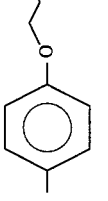 | | | 0 |
| 425 | P,R = CH$_3$ S = G Q = NHCO-⟨C$_6$H$_4$⟩-O(CH$_2$)$_5$CH$_3$ | $R_5,R_6$ = H $R_7,R_8$ = CH$_3$ | 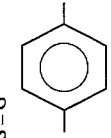 | | | 0 |
| 426 | Q,S = CH$_3$ R = G P = H | $R_5,R_6$ = H $R_7,R_8$ = CH$_3$ | 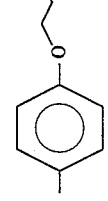 | | | 0 |

| # | | R5–R8 | | | |
|---|---|---|---|---|---|
| 427 | P,Q,R = H S = G | $R_5, R_6 = H\ R_7, R_8 = CH_3$ | H | H | $-(CH_2)_{13}CH_3$ | 0 |
| 428 | P,Q,R = H S = G | $R_5, R_6 = H\ R_7, R_8 = CH_3$ | spiro-cyclopentyl | | $-(CH_2)_9CH_3$ | 0 |
| 429 | P,Q = H R = CH_3 S = G | $R_5, R_6 = H\ R_7, R_8 = CH_3$ | H | H | $-(CH_2)_{13}CH_3$ | 0 |
| 430 | P,Q = H R = CH_3 S = G | $R_5, R_6 = H\ R_7, R_8 = CH_3$ | spiro-cyclopentyl | | $-(CH_2)_9CH_3$ | 0 |
| 431 | P,Q = H R = CH_3 S = G | $R_5, R_6 = H\ R_7, R_8 = CH_3$ | $-CH_3$ | $-CH_3$ | $-CH_2CH_2CH_2CH_2-O-C_6H_4-C(CH_3)_3$ | 0 |
| 432 | P,R = CH_3 Q = H S = G | $R_5, R_6 = H\ R_7, R_8 = CH_3$ | $-CH_3$ | $-CH_3$ | $-(CH_2)_n-CHBr-CH_3$ | 0 |
| 433 | P,R = CH_3 Q = H S = G | $R_5, R_6 = H\ R_7, R_8 = CH_3$ | $-CH_3$ | $-CH_3$ | alkyl-CH_3 | 0 |
| 434 | P,R = CH_3 Q = H S = G | $R_5, R_6 = H\ R_7, R_8 = CH_3$ | $-CH_3$ | $-CH_3$ | alkyl-CH_3 | 0 |
| 435 | P,R = CH_3 Q = H S = G | $R_5, R_6 = H\ R_7, R_8 = CH_3$ | $-CH_3$ | $-CH_3$ | alkyl-CH_3 | 0 |
| 436 | P,R = CH_3 Q = H S = G | $R_5, R_6 = H\ R_7, R_8 = CH_3$ | $-CH_3$ | $-CH_3$ | alkyl-CO_2Et | 0 |
| 437 | P,R = CH_3 Q = H S = G | $R_5, R_6 = H\ R_7, R_8 = CH_3$ | $-CH_3$ | $-CH_3$ | alkyl-phenyl | 0 |
| 438 | P,R = CH_3 Q = H S = G | $R_5, R_6 = H\ R_7, R_8 = CH_3$ | $-CH_3$ | $-CH_3$ | alkyl-phenyl | 0 |
| 439 | P,R = CH_3 Q = H S = G | $R_5, R_6 = H\ R_7, R_8 = CH_3$ | $-CH_3$ | $-CH_3$ | alkyl-phenyl | 0 |

| # | | | | | | |
|---|---|---|---|---|---|---|
| 440 | P,R = CH₃ Q = H S = G | R₅,R₆ = H R₇,R₈ = CH₃ | 1,4-diethylbenzyl-like (para-dipropyl phenyl) | —CH₃ | —CH₃ | 0 |
| 441 | P,R = CH₃ Q = H S = G | R₅,R₆ = H R₇,R₈ = CH₃ | para-substituted phenyl (isobutyl/propyl) | —CH₃ | —CH₃ | 0 |
| 442 | P,R = CH₃ Q = H S = G | R₅,R₆ = H R₇,R₈ = CH₃ | 4-pentyloxyphenyl-propyl | —CH₃ | —CH₃ | 0 |
| 443 | P,R = CH₃ Q = H S = G | R₅,R₆ = H R₇,R₈ = CH₃ | isobutyl–O–hexyl | —CH₃ | —CH₃ | 0 |
| 444 | P,R = CH₃ Q = H S = G | R₅,R₆ = H R₇,R₈ = CH₃ | isobutyl–O–heptyl | —CH₃ | —CH₃ | 0 |
| 445 | P,R = CH₃ Q = H S = G | R₅,R₆ = H R₇,R₈ = CH₃ | isobutyl–O–hexyl | —CH₃ | —CH₃ | 0 |
| 446 | P,R = CH₃ Q = H S = G | R₅,R₆ = H R₇,R₈ = CH₃ | neopentyl–O–hexyl | —CH₃ | —CH₃ | 0 |
| 447 | P,R = CH₃ Q = H S = G | R₅,R₆ = H R₇,R₈ = CH₃ | 4-methylphenoxy-undecyl (CH₃ branch) | —CH₃ | —CH₃ | 0 |
| 448 | P,R = CH₃ Q = H S = G | R₅,R₆ = H R₇,R₈ = CH₃ | cyclohexylmethyl–O–hexyl | —CH₃ | —CH₃ | 0 |
| 449 | P,R = CH₃ Q = H S = G | R₅,R₆ = H R₇,R₈ = CH₃ | phenyl–O–hexyl | —CH₃ | —CH₃ | 0 |
| 450 | P,R = CH₃ Q = H S = G | R₅,R₆ = H R₇,R₈ = CH₃ | benzyl–O–hexyl | —CH₃ | —CH₃ | 0 |
| 451 | P,R = CH₃ Q = H S = G | R₅,R₆ = H R₇,R₈ = CH₃ | isopropyl–O–CH₂CH₂–O–hexyl | —CH₃ | —CH₃ | 0 |

-continued

| | | | | |
|---|---|---|---|---|
| 452 | P,R = CH₃ Q = H S = G | R₅,R₆ = H R₇,R₈ = CH₃ | —CH₃ | —CH₃ | ~~~O~CH₃ | 0 |
| 453 | P,R = CH₃ Q = H S = G | R₅,R₆ = H R₇,R₈ = CH₃ | —CH₃ | —CH₃ | ~~~O-C₆H₄-Cl (para) | 0 |
| 454 | P,R = CH₃ Q = H S = G | R₅,R₆ = H R₇,R₈ = CH₃ | —CH₃ | —CH₃ | ~~~O-C₆H₄-C(CH₃)₃ | 0 |
| 455 | P,R = CH₃ Q = H S = G | R₅,R₆ = H R₇,R₈ = CH₃ | —CH₃ | —CH₃ | ~~~O-C₆H₄-Cl | 0 |
| 456 | P,R = CH₃ Q = H S = G | R₅,R₆ = H R₇,R₈ = CH₃ | —CH₃ | —CH₃ | ~~~O-C₆H₅ | 0 |
| 457 | P,R = CH₃ Q = H S = G | R₅,R₆ = H R₇,R₈ = CH₃ | —CH₃ | —CH₃ | ~~~O-C₆H₄-Cl | 0 |
| 458 | P,R = CH₃ Q = H S = G | R₅,R₆ = H R₇,R₈ = CH₃ | —CH₃ | —CH₃ | ~~~O-C₆H₄-CH₃ | 0 |
| 459 | P,R = CH₃ Q = H S = G | R₅,R₆ = H R₇,R₈ = CH₃ | —CH₃ | —CH₃ | ~~~O-C₆H₃(Cl)₂ | 0 |
| 460 | P,R = CH₃ Q = H S = G | R₅,R₆ = H R₇,R₈ = CH₃ | —CH₃ | —CH₃ | ~~~O-C₆H₃(CH₃)₂ | 0 |

-continued

| | | | | |
|---|---|---|---|---|
| 461 | P,R = CH₃ Q = H S = G | R₅,R₆ = H R₇,R₈ = CH₃ | —CH₃ | 4-(1-methylethyl)phenoxy-pentyl | 0 |
| 462 | P,R = CH₃ Q = H S = G | R₅,R₆ = H R₇,R₈ = CH₃ | —CH₃ | 4-nitrophenoxy-pentyl | 0 |
| 463 | P,R = CH₃ Q = H S = G | R₅,R₆ = H R₇,R₈ = CH₃ | —CH₃ | 4-aminophenoxy-pentyl | 0 |
| 464 | P,R = CH₃ Q = H S = G | R₅,R₆ = H R₇,R₈ = CH₃ | —CH₃ | 4-(N,N-dimethylamino)phenoxy-hexyl | 0 |
| 465 | P,R = CH₃ Q = H S = G | R₅,R₆ = H R₇,R₈ = CH₃ | —CH₃ | 4-chlorophenoxy-hexyl | 0 |
| 466 | P,R = CH₃ Q = H S = G | R₅,R₆ = H R₇,R₈ = CH₃ | —CH₃ | 4-methylphenoxy-hexyl | 0 |
| 467 | P,R = CH₃ Q = H S = G | R₅,R₆ = H R₇,R₈ = CH₃ | —CH₃ | 4-fluorophenoxy-heptyl | 0 |
| 468 | P,R = CH₃ Q = H S = G | R₅,R₆ = H R₇,R₈ = CH₃ | —CH₃ | 4-(N,N-dimethylamino)phenoxy-heptyl | 0 |
| 469 | P,R = CH₃ Q = H S = G | R₅,R₆ = H R₇,R₈ = CH₃ | —CH₃ | N-isopropyl-hexylamino | 0 |

-continued

| # | | | | Structure | |
|---|---|---|---|---|---|
| 470 | P,R = CH₃ Q = H S = G | R₅,R₆ = H R₇,R₈ = CH₃ | —CH₃ | tert-butyl-NH-(CH₂)₇- (N-tert-butyl-n-octylamine) | 0 |
| 471 | P,R = CH₃ Q = H S = G | R₅,R₆ = H R₇,R₈ = CH₃ | —CH₃ | 4-Cl-C₆H₄-CH₂-NH-(CH₂)₇- | 0 |
| 472 | P,R = CH₃ Q = H S = G | R₅,R₆ = H R₇,R₈ = CH₃ | —CH₃ | C₆H₅-CH₂-N(CH₃)-(CH₂)₇- | 0 |
| 473 | P,R = CH₃ Q = H S = G | R₅,R₆ = H R₇,R₈ = CH₃ | —CH₃ | 4-Cl-C₆H₄-CH₂-N(CH₃)-(CH₂)₇- | 0 |
| 474 | P,R = CH₃ Q = H S = G | R₅,R₆ = H R₇,R₈ = CH₃ | —CH₃ | piperidinyl-(CH₂)₇- | 0 |
| 475 | P,R = CH₃ Q = H S = G | R₅,R₆ = H R₇,R₈ = CH₃ | —CH₃ | 4-methylpiperazinyl-(CH₂)₇- | 0 |
| 476 | P,R = CH₃ Q = H S = G | R₅,R₆ = H R₇,R₈ = CH₃ | —CH₃ | 4-benzylpiperazinyl-(CH₂)₇- | 0 |
| 477 | P,R = CH₃ Q = H S = G | R₅,R₆ = H R₇,R₈ = CH₃ | —CH₃ | 4-benzylpiperazinyl-(CH₂)₇- | 0 |
| 478 | P,R = CH₃ Q = H S = G | R₅,R₆ = H R₇,R₈ = CH₃ | —CH₃ | 4-(4-octyloxyphenyl-carbonyl)- | 0 |

| # | | | | |
|---|---|---|---|---|
| 479 | P,R = CH₃ Q = H S = G | R₅,R₆ = H R₇,R₈ = CH₃ | H | (4-acetylphenoxy)-C₁₀H₂₁ group | 0 |
| 480 | P,R = CH₃ Q = H S = G | R₅,R₆ = H R₇,R₈ = CH₃ | H | —(CH₂)₁₃CH₃ | 0 |
| 481 | P,R = CH₃ Q = H S = G | R₅,R₆ = H R₇,R₈ = CH₃ | H | —(CH₂)₉CH₃ | 0 |
| 482 | P,R = CH₃ Q = Cl S = G | R₅,R₆ = H R₇,R₈ = CH₃ | spiro-cyclopentyl | —(CH₂)₁₃CH₃ | 0 |
| 483 | P,R = CH₃ Q = Cl S = G | R₅,R₆ = H R₇,R₈ = CH₃ | spiro-cyclopentyl | —(CH₂)₉CH₃ | 0 |
| 484 | P,R = CH₃ Q = Cl S = G | R₅,R₆ = H R₇,R₈ = CH₃ | —CH₃ | —(CH₂)₉CH₃ | 0 |
| 485 | P,R = CH₃ Q = NO₂ S = G | R₅,R₆ = H R₇,R₈ = CH₃ | —CH₃ | —(CH₂)₉CH₃ | 0 |
| 486 | P,R = CH₃ Q = NH₂ S = G | R₅,R₆ = H R₇,R₈ = CH₃ | —CH₃ | —(CH₂)₉CH₃ | 0 |
| 487 | P,R = CH₃ Q = NHCOCH₃ S = G | R₅,R₆ = H R₇,R₈ = CH₃ | —CH₃ | —(CH₂)₉CH₃ | 0 |
| 488 | P,R = CH₃ Q = OH S = G | R₅,R₆ = H R₇,R₈ = CH₃ | —CH₃ | —(CH₂)₉CH₃ | 0 |
| 489 | P,R = CH₃ Q = NHCH₃ S = G | R₅,R₆ = H R₇,R₈ = CH₃ | —CH₃ | —(CH₂)₉CH₃ | 0 |
| 490 | P,R = CH₃ Q = N(CH₃)₂ S = G | R₅,R₆ = H R₇,R₈ = CH₃ | —CH₃ | —(CH₂)₉CH₃ | 0 |
| 491 | P,R = CH₃ Q = N(CH₃)₂ S = G | R₅,R₆ = H R₇,R₈ = CH₃ | —CH₃ | —CH₃ | 0 |
| 492 | P,R = CH₃ Q = N(CH₃)₂ S = G | R₅,R₆ = H R₇,R₈ = CH₃ | H | —(CH₂)₇CH=CH(CH₂)₇CH₃ | 0 |
| 493 | P,R = CH₃ Q = N(CH₃)₂ S = G | R₅,R₆ = H R₇,R₈ = CH₃ | spiro-cyclopentyl | (4-methylphenoxy)acetyl-hexyl group | 0 |
| 494 | P,R = CH₃ Q = NHCOC(CH₃)₂(CH₂)₉CH₃ S = G | R₅,R₆ = H R₇,R₈ = CH₃ | —CH₃ | —(CH₂)₉CH₃ | 0 |
| 495 | P,R = CH₃ S = G | R₅,R₆ = H R₇,R₈ = CH₃ | —CH₃ | —CH₃ | 0 |
| 496 | P,R = CH₃ Q = NHCOC(CH₃)₂(CH₂)₉CH₃ S = G | R₅,R₆ = H R₇,R₈ = CH₃ | —CH₃ | —CH₃ | 0 |
| 497 | P,R = CH₃ Q = NHCOC(CH₃)₂(CH₂)₁₀CH₃ S = G | R₅,R₆ = H R₇,R₈ = CH₃ | —CH₃ | —CH₃ | 0 |
| 498 | P,R = CH₃ Q = NH(CH₂)₉CH₃ S = G | R₅,R₆ = H R₇,R₈ = CH₃ | —CH₃ | branched heptyl | 0 |
| 499 | P = H Q = NHCO(CH₂)₁₀CH₃ R = CH₃ S = G | R₅,R₆ = H R₇,R₈ = CH₃ | H | —(CH₂)₁₀CH₃ | 0 |

| # | P, Q, R, S | R5–R8 | | | |
|---|---|---|---|---|---|
| 500 | P = H Q = NHCO(CH₂)₈CH₃ R = CH₃ S = G | R₅,R₆ = H R₇,R₈ = CH₃ | —CH₃ | —CH₃ | O |
| 501 | P = H Q = NHCOC(CH₃)₂(CH₂)₉CH₃ R = CH₃ S = G | R₅,R₆ = H R₇,R₈ = CH₃ | —CH₃ | —(CH₂)₉CH₃ | O |
| 502 | P,Q = H R = OCH₃ S = G | R₅,R₆ = H R₇,R₈ = CH₃ | —CH₃ | —(CH₂)₉CH₃ | O |
| 503 | P,Q = H R = O(CH₂)₉CH₃ S = G | R₅,R₆ = H R₇,R₈ = CH₃ | —CH₃ | —(CH₂)₉CH₃ | O |
| 504 | P = CH₃ Q = H R = OCH₃ S = G | R₅,R₆ = H R₇,R₈ = CH₃ | —CH₃ | —(CH₂)₉CH₃ | O |
| 505 | P,Q = H R = O(CH₂)₉CH₃ S = G | R₅,R₆ = H R₇,R₈ = CH₃ | —CH₃ | —CH₃ | O |
| 506 | P,Q = H R = O(CH₂)₆O—⟨C₆H₄⟩—Cl S = G | R₅,R₆ = H R₇,R₈ = CH₃ | —CH₃ | H | O |
| 507 | P = H Q = COCH₃ R = OCH₃ S = G | R₅,R₆ = H R₇,R₈ = CH₃ | —CH₃ | —(CH₂)₉CH₃ | O |
| 508 | P = H Q = COCH₃ R = OCH₃ S = G | R₅,R₆ = H R₇,R₈ = CH₃ | —CH₃ | —CH(CH₂)...  | O |
| 509 | P = H Q = CH₂CH₃ R = OCH₃ S = G | R₅,R₆ = H R₇,R₈ = CH₃ | —CH₃ | —(CH₂)₉CH₃ | O |
| 510 | P = H Q = COCH₂O(CH₂)₉CH₃ | R₅,R₆ = H R₇,R₈ = CH₃ | —CH₃ | —CH₃ | O |
| 511 | P = H Q = CO(CH₂)₁₀CH₃ R = OCH₃ S = G | R₅,R₆ = H R₇,R₈ = CH₃ | —CH₃ | —CH₃ | O |
| 512 | P = H Q = NO₂ R = OCH₃ S = G | R₅,R₆ = H R₇,R₈ = CH₃ | —CH₃ | —(CH₂)₉CH₃ | O |
| 513 | P = H Q = N(CH₃)₂ S = G | R₅,R₆ = H R₇,R₈ = CH₃ | —CH₃ | —CH₃ | O |
| 514 | P = H Q = N(CH₃)₂ S = G R = O(CH₂)₆O—⟨C₆H₄⟩—Cl | | —CH₃ | —CH₃ | O |
| 515 | P = H Q = N(CH₃)₂ R = OCH₃ S = G | R₅,R₆ = H R₇,R₈ = CH₃ | —CH₃ | —(CH₂)₉CH₃ | O |
| 516 | P = H Q = NHCOC(CH₃)₃ R = OCH₃ S = G | R₅,R₆ = H R₇,R₈ = CH₃ | —CH₃ | —CH₃ | O |
| 517 | P = H Q = N(CH₃)₂ R = OCH₃ | R₅,R₆ = H R₇,R₈ = CH₃ | —CH₃ | —CH₃ | O |
| 518 | P,R = CH₃ Q = OCOCH(CH₃)₂ S = G | | —CH₃ | —CH₃ | O |

The compounds having the above-mentioned formula (I) include some known compounds and novel compounds represented by the formula (Ia). The novel compounds can also be produced according to production processes used in the production of the known compounds. Preferably, they can be produced by a novel production process proposed as one aspect of the present invention.

For example, the compounds having the formula (I) can be produced by the following respective reaction schemes.

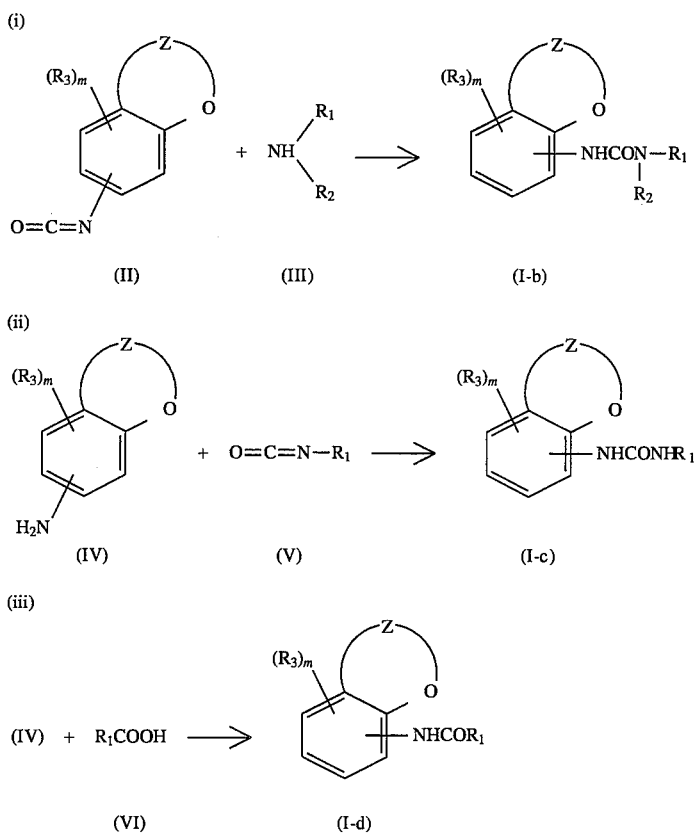

wherein $R_1$, $R_2$, $R_3$, Z and m are as defined above.

The reactions represented by the reaction schemes (i) and (ii) can be practiced by reacting the corresponding amine compound represented by the formula (III) or (IV) with an isocyanate compound represented by the formula (II) or (V) in the absence or presence of a solvent.

Most of the compounds represented by the formulae (II) to (VI) are known compounds and can be produced by known processes. The novel compounds can be produced according to the processes for producing the known compounds. For example, 2,3-dihydrobenzofuranylamine which is a compound belonging to the compounds represented by the formula (IV) can be produced a process described in Chem. Abst., 66, 463196 (1969).

In general, with respect to the amount ratio of reactants (starting compounds) used in the reaction, the amount of the amine compound and the amount of the isocyanate compound are preferably set so as to be equivalent to each other. However, the optimal amount ratio varies depending upon the reactants used. A person having ordinary skill in the art can learn the optimal amount ratio through a simple small-scale experiment. In general, the amount of the isocyanate compound can be varied in the range of from 0.2 to 5 equivalents based on one equivalent of the amine compound.

The reaction solvent may be any type of solvent so far as it has no adverse effect on the reaction. Examples of the solvent generally used in the reaction include halogenated hydrocarbons, such as dichloromethane and chloroform, aromatic hydrocarbons, such as benzene and toluene, ethers, such as diethyl ether and tetrahydrofuran, esters, such as ethyl acetate, and aprotic polar solvents, such as dimethylformamide and dimethylsulfoxide.

With respect to the reaction conditions, the reaction temperature is in the range of from −20° to 150° C., preferably in the range of from room temperature to 100° C., and the reaction time is usually 72 hrs or less.

After the completion of the reaction, the reaction mixture may be subjected to conventional separation and purification procedure, that is, extraction, recrystallization, chromatography, etc. to isolate an intended benzoxa condensed ring compound represented by the formula (I-b) or (I-c). Further, the product can be converted to a pharmaceutically acceptable salt by a conventional method.

The reaction corresponding to the reaction scheme (iii) is a reaction of an amine compound represented by the formula (IV) with a reactive derivative of a carboxylic acid represented by the formula (IV). Among the compounds represented by the formula (I), compounds belonging to the above-mentioned amide derivatives can be efficiently produced by this reaction.

This reaction can be practiced according to a known reaction of an amino compound with a carboxylic acid or a reactive derivative of the carboxylic acid. The reactive derivative of a carboxylic acid used in the invention embraces all reactive derivatives of carboxylic acids usually known in the field of organic synthesis including acid anhydrides, acid halides and mixed acid anhydrides of the corresponding carboxylic acids.

Accordingly, the above-mentioned reaction can be practiced by reacting the amine compound with 1 to 5 equivalents of the corresponding carboxylic acid chloride or acid anhydride in the presence of a solvent.

The reaction temperature is in the range of from −20° to 150° C., preferably in the range of from −10° to 100° C., and the reaction time is usually 72 hrs or less.

Examples of the reaction solvent include halogenated hydrocarbons, such as dichloromethane and chloroform, aromatic hydrocarbons, such as benzene and toluene, ethers, such as diethyl ether and tetrahydrofuran, esters, such as ethyl acetate, and aprotic polar solvents, such as dimethylformamide and dimethylsulfoxide. In this case, 0.1 to 10 equivalents of a basic amine compound, for example, triethylamine, pyridine or 4-dimethylaminopyridine, may be added to the reaction system.

After the completion of the reaction, the reaction mixture may be subjected to conventional separation and purification procedure, that is, extraction, recrystallization, chromatography, etc. to isolate an intended benzoxa condensed ring compound represented by the formula (I-d).

As specifically mentioned above, the compound represented by the formula (I) or the compound represented by the formula (Ia) can bear, in its molecule, an amino group or a carboxyl group. Therefore, if necessary, these compounds can be converted to their acid addition salts or alkali addition salts by a conventional salt forming reaction.

For example, with respect to the compound bearing an amino group represented by the formula (I), a salt forming reaction can be practiced by simply mixing the corresponding compound represented by the formula (I) with an inorganic acid or an organic acid in the absence or presence of a suitable solvent. The inorganic acid or organic acid used in the salt forming reaction may be any one so far as it can produce a pharmaceutically acceptable salt upon being reacted with the compound represented by the formula (I). Favorable examples of the inorganic acid or organic acid include mineral acids, such as hydrochloric acid, hydrobromic acid, sulfuric acid, phosphoric acid and carbonic acid, and organic acids, such as citric acid, malic acid, oxalic acid, tartaric acid, fumaric acid and methanesulfonic acid.

The compound represented by the formula (I) and its pharmaceutically acceptable salt provided by the present invention have an ACAT enzyme inhibitory activity and an excellent pharmacological activity for lowering the total cholesterol and LDL levels of the blood, liver and arterial wall, which renders them useful for the suppression of the progress or regression of hyperlipidemia and atherosclerosis.

The benzoxa condensed ring compound and its pharmaceutically acceptable salt according to the present invention can be blended with a pharmacologically acceptable carrier to provide a pharmaceutical composition. Although the content of the active ingredient in the pharmaceutical composition is not particularly limited, it is usually in the range of from 5 to 70% by weight.

The compound represented by the formula (I) and its pharmaceutically acceptable salt provided by the present invention can be orally administered.

Examples of dosage forms of the oral preparation include a tablet, a powder, granules and a capsule.

These dosage forms can be shaped according to a conventional method through the use of, for example, an excipient, such as lactose, starch or crystalline cellulose, a binder, such as carboxymethylcellulose, methyl cellulose or polyvinyl pyrrolidone, and a disintegrator, such as sodium alginate, sodium hydrogencarbonate or sodium laurate. The powder and granules as well can be shaped in a similar manner. The capsule can be shaped by filling a capsule, such as gelatin, with a powder or granules. Examples of parenteral preparations include percutaneous preparations, such as a suppository, a patch and an injection.

Although the dose of the compound represented by the formula (I) and its pharmaceutically acceptable salt provided by the present invention varies depending upon the severity of disease, age and sex of patient, it is usually about 1 to 500 mg/day/adult.

EXAMPLES

The present invention will now be described in more detail with reference to, but is by no means limited to, the following Examples.

REFERENCE EXAMPLE 1

Synthesis of 2-amino-6-nitrophenol 100 ml of methanol was added to 5.0 g of 2,6-dinitrophenol in a vessel. The inside of the vessel was purged with argon. About 1.5 g of 10% palladium-carbon was added thereto, the inside of the vessel was purged with argon and then with hydrogen, and the reaction mixture was stirred at room temperature overnight.

After the completion of the reaction, the palladium-carbon was removed by filtration with Celite, and the filtrate was concentrated to provide 4.1 g of the title compound, that is, 2-amino-6-nitrophenol.

$^1$H NMR (CDCl$_3$) δ (ppm): 10.70 (s, 1H, OH), 7.46(dd, J=2.0Hz, 8.2Hz, 1H, ArH), 6.94(dd, J=2.0Hz, 7.7Hz, 1H, ArH), 6.76(dd, J=8.2Hz, 7.7Hz, 1H, ArH), 3.70–4.50(br, 2H, NH$_2$)

REFERENCE EXAMPLE 2

Preparation of trimethylsilyl polyphosphate solution (PPSE)

50 ml of 1,2-dichlorobenzene was added to 10 g of phosphorus pentaoxide, and 25 ml of hexamethyldisiloxane was added to the mixture with stirring. The mixture was allowed to react under reflux for 10 min and cooled to room temperature to prepare the title solution.

REFERENCE EXAMPLE 3

Synthesis of 7-nitro-2-(3-pyridyl)benzoxazole 15 ml of the trimethylsilyl polyphosphate solution prepared in Reference Example 2 was placed in a vessel purged with argon, and 1.06 g of 2-amino-6-nitrophenol prepared in Reference Example 1 and 0.62 g of nicotinic acid. The mixture was allowed to react under reflux for 3 hr. After the completion of the reaction, 50 ml of a 1 N aqueous sodium hydroxide solution was added to the reaction mixture. The intended product was extracted with dichloromethane (50 ml×3), and the organic layer was washed with water and then dried. The organic solvent was removed by evaporation, and the resultant concentrate was purified by silica gel column chromatography (hexane:ethyl acetate=6:4) to provide 0.49 g of the title compound.

$^1$H NMR (CDCl$_3$) δ (ppm): 9.40(d, J=1.5Hz, 1H, ArH), 8.87(dd, J=4.8Hz, 1.5Hz, 1H, ArH), 8.58(ddd, J=1.8Hz, 2.2Hz, 7.9Hz, 1H, ArH), 8.34 (dd, J=2.2Hz, 1.1Hz, 1H, ArH), 8.27 (d, J=1.1Hz, 1H, ArH), 7.58–8.24(m, 2H, ArH)

REFERENCE EXAMPLE 4

Synthesis of 7-amino-2-(3-pyridyl)benzoxazole 4 ml of 10% acetic acid was added to 7-nitro-2-(3-pyridyl)benzoxazole prepared in Reference Example 3, and 200 mg of powdered iron was added by portions with stirring at room temperature. The mixture was heated to 100° C. in an oil bath and stirred for 2 hr. The reaction mixture was filtered through Celite and washed with a small amount of dilute hydrochloric acid. The filtrate was neutralized with an aqueous sodium hydroxide solution, the product was extracted with ethyl acetate, and the organic layer was dried. The organic solvent was removed by evaporation to provide 153 mg of the intended title compound.

$^1$H NMR (δ/ppm, d$_6$-DMSO) 9.37 (dd, J=0.9Hz, 2.2Hz, 1H, ArH), 8.78 (dd, J=1.8Hz, 4.8Hz, 1H, ArH), 8.59 (ddd, J=1.8Hz, 2.2Hz, 8.1Hz, 1H, ArH), 7.63(ddd, J=0.9Hz, 4.8Hz, 8.1Hz, 1H, ArH), 6.92–7.10 (m, 2H, ArH), 6.67 (dd, J=1.8Hz, 7.3Hz, 1H, ArH), 5.59(s, 2H, NH$_2$)

REFERENCE EXAMPLE 5

Synthesis of 2-phenylbenzoxazolyl-7-isocyanate 137 mg of 7-amino-2-phenylbenzoxazole was suspended in 5 ml of 1,2-dichlorobenzene, and the mixture was stirred under reflux for 10 min. The reaction mixture was somewhat cooled. 129 mg of triphosgene and 132 mg of triethylamine were added thereto, and the mixture, as such, was stirred for 20 min.

After the completion of the reaction, the reaction mixture was filtered through Celite to remove insolubles. The solvent was removed by evaporation to provide 154 mg of the intended title compound.

EXAMPLE 1

Synthesis of 1-(2-phenylbenzoxazol-7-yl)-3-[(1-phenylcyclopentyl)methyl] urea (105)

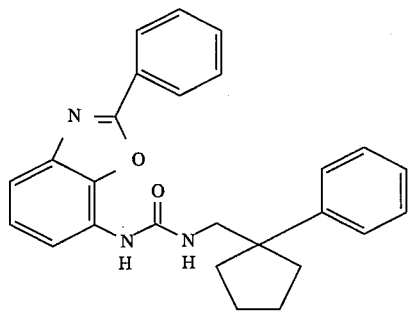

A 77 mg amount of 2-phenylbenzoxazolyl-7-isocyanate prepared in Reference Example 5 was dissolved in 3 ml of ethyl acetate, 57 mg of 1-phenylcyclopentylmethylamine was added thereto, and the mixture was stirred at room temperature overnight.

After the completion of the reaction, the solvent was removed by evaporation. The resultant precipitate was recrystallized from hexane-ethyl acetate to provide 71 mg of the intended title compound.

$^1$H NMR (CDCl$_3$) δ (ppm): 8.16–8.27(m, 2H, A/H), 7.44–7.59(m, 4H, ArH), 7.13– 7.41 (m, 9H, A/H), 6.35(s, 1H, NH), 4.49(br, 1H, NH), 3.47(d, J=5.7Hz, 2H, —CH$_2$—), 1.70–2.10(br, 8H, —CH$_2$—) m.p.: 214°–215° C.

EXAMPLE 2

Synthesis of N-[2-(3-pyridyl)benzoxazol-7-yl]-1-decylcyclopentanecarboxamide (207)

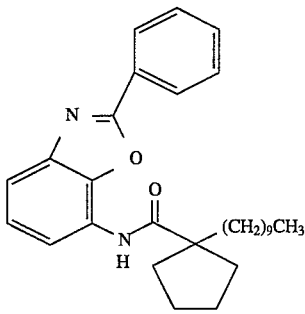

A 65 mg amount of 1-decylcyclopentanecarboxylic acid chloride was added to a solution of 51 mg of 7-amino-2-(3-pyridyl)benzoxazole and 0.034 ml of triethylamine in 2.5 ml of dichloromethane, and the mixture was stirred at room temperature for 9 hrs.

A saturated aqueous potassium hydrogensulfate solution (10 ml) was added to the reaction mixture, and the mixture was extracted with ethyl acetate (20 ml×2).

The extract was dried over anhydrous magnesium sulfate, filtered, concentrated and then purified by thin-layer chromatography (hexane:ethyl acetate=1:1) to provide 35 mg of the intended title compound.

Property Values: $^1$H NMR (CDCl$_3$) δ (ppm): 9.45(dd, J=2.2Hz, 0.7Hz, 1H, ArH), 8.79(dd, J=4.8Hz, 1.8Hz, 1H, ArH), 8.51 (ddd, J=7.9Hz, 2.2Hz, 1.8Hz, 1H, ArH), 8.08 (dd, J=7.9Hz, 1.3Hz, 1H, ArH), 7.34–7.63(m, 4H, ArH, ArNH), 2.20–2.34(br-t, J=6.4Hz, 2H, —CH$_2$—), 1.53–1.90(m, 8H, —CH$_2$—), 1.20–1.47 (m, 16H, —CH$_2$—), 0.84 (t, J=5.1Hz, —CH$_3$)

REFERENCE EXAMPLE 6

Synthesis of 5-chloro-2,2,4,6-tetramethyl-7-nitro-2,3-dihydrobenzofuran

A 50 g amount of 4-chloro-3,5-xylenol was dissolved in 50 ml of dry methanol. A 73.9 g amount of sodium methoxide (28% methanol solution) and 43.4 g of 3-chloro-2-methyl-1-propene was added thereto, and the mixture was heated under reflux with stirring for 28 hrs. The reaction mixture was cooled, the solvent was removed by evaporation, 300 ml of water was added to the residue, and the mixture was extracted with ethyl acetate (150 ml× three times). The organic layer was washed with a 5N aqueous sodium hydroxide solution (70 ml×two times), water and brine and dried over anhydrous magnesium sulfate, and the solvent was removed by evaporation to provide 66.6 g of a pale yellow oleaginous substance. A 25 g amount of anhydrous magnesium chloride was added to the oleaginous substance, and the mixture was heated at 200° C. with stirring for 24 hrs. The reaction mixture was cooled, 500 ml of water was added thereto, and the mixture was extracted with methylene chloride (250 ml× three times). The organic layer was washed with a 5N aqueous sodium hydroxide solution (100 ml), a 1N aqueous hydrochloric acid solution (100 ml) and brine in that order and dried over anhydrous magnesium sulfate, and the solvent was removed by evaporation to provide 64.8 g of a pale green oleaginous substance.

Then, this product was dissolved in 300 ml of acetic anhydride, and 29.09 g of nitric acid (70%) was slowly added thereto under ice cooling. The stirring was continued for additional one hour to precipitate crystal. The reaction was allowed to proceed at room temperature for additional 2 hr, the reaction mixture was poured into 500 ml of water, and the mixture was extracted with ethyl acetate (300 ml×3 times). The organic layer was washed with an aqueous sodium hydroxide solution (2N, 200 ml× 2 times), water and saturated saline in that order and dried over anhydrous magnesium sulfate, and the solvent was removed by evaporation to provide pale brown crystals. This crystal was dissolved in 350 ml of hexane with heating, insolubles were removed by filtration, and the filtrate was subjected to recrystallization. The resultant crystals were further recrystallized from ethanol to provide 31.4 g of the intended compound (5-chloro- 2,2,4,6-tetramethyl-7-nitro-2,3-dihydrobenzofuran) as pale yellow crystals (yield: 38.5%). The melting point (m.p.) was 111° to 112° C.

REFERENCE EXAMPLE 7

Synthesis of 7-amino -2,2,4,6-tetramethyl-2,3-dihydrobenzofuran hydrochloride

A 20.00 g amount of 5-chloro-2,2,4,6-tetramethyl-7-nitro-2,3-dihydrobenzofuran was dissolved in 300 ml of ethyl acetate, 2.0 g of Pd-C (10%) was added thereto, and the mixture was subjected to hydrogenation at room temperature under a hydrogen gas pressure of one arm with vigorous stirring. After 24 hrs from the initiation of the hydrogenation, the consumption of hydrogen gas was about 6 liters. A 30 ml amount of triethylamine, 4.0 g of Pd-C (10%) and 100 ml of ethanol were added thereto, and the hydrogenation was continued for additional 24 hrs. After the completion of the reaction was confirmed by TLC, Pd-C was removed by filtration and the solvent was removed by evaporation. A 300 ml amount of water was added to the resultant solid, and the mixture was extracted with ethyl acetate (150 ml×3 times). The organic layer was washed with an aqueous sodium hydroxide solution (1N, 100 ml×2 times), water (100 ml) and brine (50 ml) in that order and dried over anhydrous magnesium sulfate, the solvent was removed by evaporation, and the residue was sufficiently dried to provide pale brown crystals. These crystals were dissolved in 100 ml of ethanol, about 40 ml of an ethanol solution (7N) of hydrochloric acid was added thereto, and the solvent was removed by distillation to provide a crude hydrochloride. The crude hydrochloride was dissolved in 50 ml of methylene chloride with heating, insolubles were removed by filtration, and 400 ml of ethyl acetate was added to the filtrate with heating to effect recrystallization. The resultant crystal was collected by filtration, washed with a small amount of ethyl acetate and then dried to provide 14.47 g of the intended product, i.e., 7-amino-2,2,4,6-tetramethyl-2,3-dihydrobenzofuran hydrochloride. The yield was 72%.

Colorless plate crystal m.p.: 176°–178° C. (sublimable) $^1$H NMR (CDCl$_3$) δ (ppm): 6.45 (s, 1H), 3.47(s, 3H), 2.91(s, 2H), 2.57(s, 3H), 2.13(s, 3H), 1.49(s, 6H)

REFERENCE EXAMPLE 8

Synthesis of 2,2,6-trimethyl-2,3-dihydrobenzofuran-7-yl isocyanate

A 400 mg amount of 7-amino -2,2,6-trimethyl-2,3-dihydrobenzofuran was dissolved in 10 ml of carbon tetrachloride, and 246 mg of triphosgene was added thereto. The reaction solution was heated to 80° C., and 229 mg of triethylamine was slowly added thereto with stirring. Further, the mixture was heated under reflux for 1.5 hr. The reaction mixture was filtered through Celite to remove insolubles. The solvent was removed by evaporation to provide 461 mg of the title compound.

$^1$H NMR(CDCl$_3$) δ (ppm): 6.82 (d, 1H, J=7.5Hz), 6.59 (d, 1H, J=7.5Hz), 3.02 (s, 2H), 2.2–4(s, 3H), 1.50(s, 6H)

EXAMPLE 3

Synthesis of 1-[(1-phenylcyclopentyl)methyl-3-(2,2,6-trimethyl-2,3-dihydrobenzofuran-7-yl)urea (309)

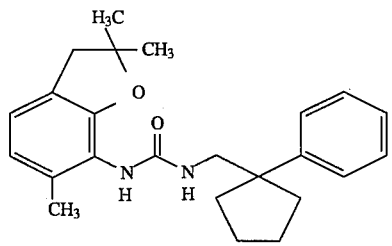

A 60 mg amount of (1-phenycyclopentyl)methylamine was added to a solution of 70 mg of 2,2,6-trimethyl-2,3-dihydrobenzofuran- 7-yl isocyanate in 2 ml of ethyl acetate, and the mixture was stirred at room temperature for 15 hrs. The solvent was removed by evaporation under reduced pressure, and the residue was subjected to recrystallization to provide 65 mg of the intended title compound.

Property values $^1$H NMR (CDCl$_3$) δ (ppm): 7.0–7.2(m, 5H), 6.95(d, 1H, J=9Hz), 6.65(d, 1H, J=9Hz), 5.4 (br-s, 1H), 4.3 (br-s, 1H), 3.2–3.4 (m, 2H), 2.93(s, 3H), 2.14(s, 3H), 1.5–2.1(m, 8H), 1.52 (s, 6H) m.p.: 186°–186.5° C.

EXAMPLE 4

Synthesis of N-(2,2,6-trimethyl-2,3-dihydrobenzofuran- 7-yl)hexadecaneamide (429)

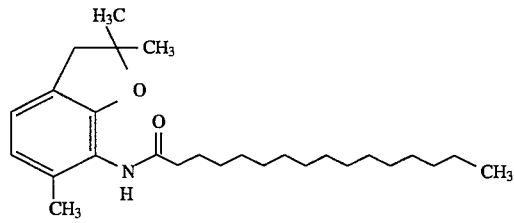

A 171 mg amount of hexadecanecarboxylic acid chloride was added to a solution of 100 mg of 7-amino- 2,2,6-trimethyl-2,3-dihydrobenzofuran and 63 mg of triethylamine in 2 ml of dichloromethane, and the mixture was stirred at room temperature for one hour. A 10 ml amount of a saturated sodium hydrogencarbonate solution was added thereto, and the mixture was extracted twice with 20 ml of ethyl acetate.

The extract was dried over anhydrous magnesium sulfate, filtered, concentrated and purified by column chromatography (hexane/ethyl acetate) to provide 193 mg of the intended title compound.

¹H NMR (CDCl₃) δ (ppm): 6.95(d, 1H, J=9Hz), 6.68(d, 1H, J=9Hz), 6.7(br-s, 1H), 2.99(s, 2H), 2.4(br-s, 2H), 2.19(s, 3H), 1.66(br-t, 2H, J=9Hz), 1.44(s, 6H), 1.05–1.5(m, 24H), 0.89(br-t, 3H, J=5Hz) m.p. 76°–76.5° C.

EXAMPLE 5

Synthesis of N-(2,2,4,6-tetramethyl-2,3-dihydrobenzofuran- 7-yl)-2,2-dimethyldodecaneamide (434)

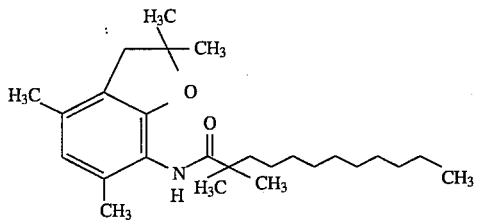

A 233 mg amount of 7-amino -2,2,4,6-tetramethyl-2,3-dihydrobenzofuran hydrochloride was dissolved in 3 ml of dichloromethane, and 0.28 ml of triethylamine was added thereto. 248 mg of 2,2-dimethyldodecanecarboxylic acid chloride was slowly added thereto, and the mixture was stirred at room temperature for 15 hrs. A 15 ml amount of 2N hydrochloric acid was added thereto, the resultant dichloromethane layer was separated, and the water layer was further extracted with ethyl acetate (25 ml×three times). The organic layers were combined with each other and washed with water and brine in that order. Anhydrous magnesium sulfate was added thereto to dry the washed organic layer. The solvent was removed by evaporation to provide 413 mg of the title compound. This product was purified by silica gel chromatography (hexane/ethyl acetate) to provide 370 mg of a colorless crystal. The yield was 92%.

¹H NMR (CDCl₃) δ (ppm): 6.79(bs, 1H), 6.50(s, 1H), 2.89(s, 2H), 2.14(s, 3H), 2.13(s, 3H), 1.5–1.6(m, 2H), 1.43(s, 6H), 1.2– 1.5(m, 22H), 0.88(t, 3H, J=6.6Hz) m.p.: 57°–58.5° C.

EXAMPLE 6

Synthesis of N-(2,2,4,6-tetramethyl-5-nitro-2,3-dihydrobenzofuran- 7-yl)-2,2-dimethyldodecaneamide (485)

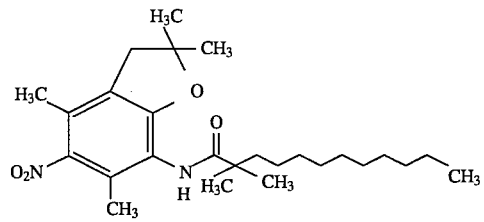

A 64 mg amount of N-(2,2,4,6-tetramethyl-2,3-dihydrobenzofuran- 7-yl)-2,2-dimethyldodecaneamide (434) was dissolved in 0.5 ml of acetic anhydride, and 24 mg of nitric acid was slowly added to the solution while cooling the solution to 0° C. The mixture, as such, was allowed to react at 0° C. for one hour with stirring. The reaction solution was diluted with 5 ml of ice-cold water, 10 ml of a saturated aqueous sodium hydrogencarbonate solution was added thereto to effect neutralization, and the mixture was extracted with ethyl acetate (20 ml×twice). The organic layer was washed with water and brine in that order and dried over anhydrous magnesium sulfate. The solvent was removed by evaporation, and 72 mg of the resultant crude product was purified by silica gel column chromatography (hexane/ethyl acetate) to provide 56 mg of the intended title compound. The yield was 78%.

¹H NMR (CDCl₃) δ (ppm): 6.80(br-s, 1H), 2.97(s, 2H), 2.15(s, 3H), 2.11(s, 3H), 1.5–1.6(m, 2H), 1.47(s, 6H), 1.2–1.5(m, 22H), 0.88 (t, 3H, J=6.5Hz) Pale yellow crystal m.p.: 88°–90° C. (recrystallized from hexane)

EXAMPLE 7

Synthesis of N-(5-amino-2,2,4,6-tetramethyl-2,3-dihydrobenzofuran- 7-yl)-2,2-dimethyldodecaneamide (486)

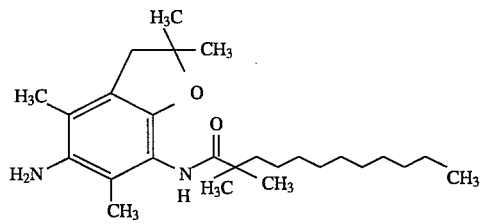

A 2.0 g amount of N-(2,2,4,6-tetramethyl-5-nitro- 2,3-dihydrobenzofuran-7-yl)-2,2-dimethyldodecaneamide (485) was dissolved in 30 ml of ethanol, 600 mg of Pd-C (10%) was added thereto, and the mixture was subjected to hydrogenation at room temperature with vigorous stirring. After 24 hrs from the initiation of the hydrogenation, the reaction was completed. Pd-C was removed by filtration with Celite, and the solvent was removed by evaporation to provide 1.75 g of the intended title compound as a solid. The yield was 94%.

¹H NMR (CDCl₃) δ (ppm): 6.86(br-s, 1H), 3.26(br-s, 2H), 2.92(s, 2H), 2.15(s, 3H), 2.04(s, 3H), 1.5–1.65(m, 2H), 1.40(s, 6H), 1.2–1.5(m, 22H), 0.88(t, 3H, J=6.5Hz) m.p.: 125° C. (recrystallized from hexane and dichloromethane)

EXAMPLE 8

Synthesis of N-(5-dimethylamino -2,2,4,6-tetramethyl- 2,3-dihydrobenzofuran-7-yl)-2,2-dimethyldodecaneamide (490)

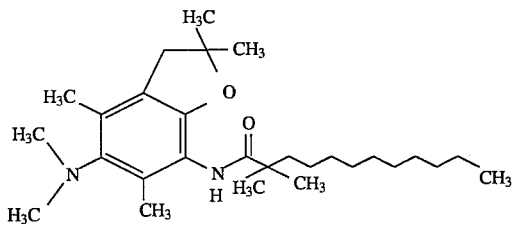

A 1.75 g amount of N-(5-amino-2,2,4,6-tetramethyl- 2,3-dihydrobenzofuran-7-yl)-2,2-dimethyldodecaneamide (486) was dissolved in 30 ml of ethanol, 4.26 g of a formaldehyde solution (37%) and 600 mg of platinum dioxide were added thereto, and the mixture was subjected to hydrogenation at room temperature. After 7 hrs from the initiation of the hydrogenation, the catalyst was removed by filtration with Celite, and the solvent was removed by evaporation. A 50 ml amount of water was added to the residue, and the mixture was extracted with ethyl acetate (30 ml×three times). The organic layer was washed with water and brine and dried over anhydrous magnesium sulfate. The solvent was removed by distillation to provide 2.25 g of a light brown oleaginous substance. The oleaginous substance was purified by silica gel column chromatography (hexane/ethyl acetate) to provide 1.33 g of the intended title compound. The yield was 71.4%.

$^1$H NMR (CDCl$_3$) δ (ppm): 6.82(br-s, 1H), 2.89(s, 2H), 2.79(s, 6H), 2.10(s, 1.2–1.5(m, 22H), 0.88(t, 3H, J=6.6Hz) Colorless crystal m.p.: 84.5°–85° C.

EXAMPLE 9

Synthesis of N-(5-dimethylamino-2,2,4,6-tetramethyl- 2,3-dihydrobenzofuran-7-yl)-2,2-dimethyl-dodecaneamide hydrochloride (490 hydrochloride)

A 452 mg amount of free base of the compound (490) prepared in Example 8 was dissolved in 3 ml of ethanol, and 1 ml of ethanol saturated with hydrochloric acid was added thereto to convert the compound to a hydrochloride. The solvent was removed by evaporation, and the resultant crystal was recrystallized from ethyl acetate to provide 313 mg of the intended title compound.

$^1$H NMR(CDCl$_3$) δ (ppm): 6.85(br-s, 1H), 3.4(br-s, 6H), 2.97(s, 2H), 2.65(br-s, 3H), 2.42(br-s, 3H), 1.2–1.65(m, 30H), 0.88(t, 3H, J=6.5Hz) Colorless crystal m.p.: 107°–110° C.

EXAMPLE 10

Synthesis of N-(2,2,4,6-tetramethyl-2,3-dihydrobenzofuran- 7-yl)-[2,2-dimethyl-7-(4-nitrophenyloxy)] heptaneamide (462)

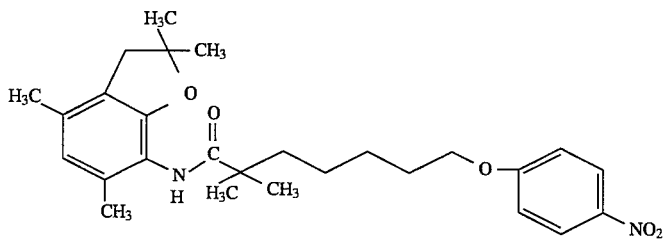

A 410 mg amount of N-(2,2,4,6-tetramethyl-2,3-dihydrobenzofuran- 7-yl)-(2,2-dimethyl-7-bromo)heptaneamide prepared according to a method described in Example 5 was dissolved in 10 ml of acetonitrile together with 139 mg of p-nitrophenol and mg of potassium carbonate, and the resultant solution 138 was heated under reflux for 2.5 hr. The solvent was removed by evaporation, 30 ml of a 5N aqueous sodium hydroxide solution was added to the residue, and the mixture was extracted with 100 ml of ethyl acetate. The organic layer was washed with 5N sodium hydroxide, 1N hydrochloric acid, water and brine in that order and then dried over anhydrous magnesium sulfate. The solvent was removed by evaporation to provide 484 mg of an oleaginous substance which was then purified by silica gel column chromatography to provide 354 mg of the intended title compound.

Pale yellow crystal $^1$H NMR(CDCl$_3$) δ (ppm): 8.17(d, 2H, J=9.3Hz), 6.91(d, 2H, J=9.3Hz), 6.8(br-s, 1H), 6.49(br-s, 1H), 4.04(t, 2H, J=6.5Hz), 2.88(s, 2H), 2.13(s, 6H), 1.25–2.0(m, 20H) m.p.: 93°–94° C.

EXAMPLE 11

Synthesis of N-(2,2,4,6-tetramethyl-2,3-dihydrobenzofuran- 7-yl)-2,2-dimethyl-8-(N-isopropyl)aminooctaneamide (469)

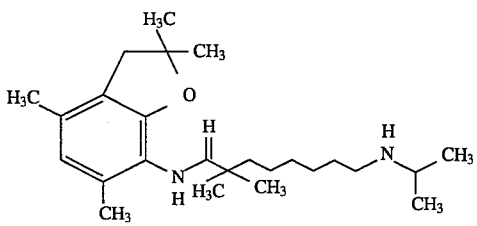

A 203 mg amount of N-(2,2,4,6-tetramethyl-2,3-dihydrobenzofuran- 7-yl)-2,2-dimethyl-8-bromooctaneamide and 150 mg of potassium carbonate were added to 7 ml of isopropylamine, and the mixture was allowed to react under reflux for 14 hrs.

After the completion of the reaction, excess isopropylamine was removed by distillation under reduced pressure. Ethyl acetate and 2N hydrochloric acid were added to the residue, followed by separation. A 2N aqueous sodium hydroxide solution was added the water layer to render the solution basic, and the liberated compound was extracted with ethyl acetate.

The organic solvent was removed by distillation under reduced pressure to provide 54 mg of the title compound.

$^1$H NMR (CDCl$_3$) δ (ppm): 6.79(br, 1H), 6.48(s, 1H), 3.19(br, 1H), 2.88(s, 2H), 2.61(t, J=7.0Hz 2H), 2.13(s, 6H), 1.42(s, 6H), 1.27(s, 6H), 1.28–1.65(m, 10H), 1.10(d, J=6.2Hz 6H)

Preparation of hydrochloride

Hydrochloric acid/ether was added to 54 mg of the title compound until a precipitate did not occur any longer. The precipitate was collected by filtration and subjected to recrystallization from ethyl acetate to provide 30 mg of a hydrochloride of the title compound.

Property value m.p.: 129°–130° C.

EXAMPLES 12 TO 86

Compounds of the present invention were synthesized in the same manner as that of Examples 1 to 11, except that respective corresponding starting compounds and reactants were used. Property values thus produced are given in the following Table 1. Compound Nos. described in Table 1 represent respective numbers given to the compounds listed above as favorable specific examples.

TABLE 1

|  | Compound No. | $^1$H NMR Data (CDCl$_3$) δ (ppm) | Yield (%) | m.p. (°C.) | Synthetic method |
|---|---|---|---|---|---|
| Example 12 | 106 | 8.16–8.28(m, 2H), 7.30–7.74(m, 6H), 6.55(s, 1H), 4.86(br-s, 1H), 3.31(m, 2H), 1.16–1.73(m, 20H), 0.87 (t, 3H, J=5.3Hz) | 68 | 130–132 | According to Example 1 |
| Example 13 | 107 | 8.18–8.29(m, 2H), 7.49–7.56(m, 4H), 6.88–7.02(m, 5H) 5.86(br-s, 1H), 4.03(br-t, 1H, J=5.7Hz), 3.33(d, 2H, J=5.7Hz), 2.34(s, 3H), 2.15(s, 3H), 1.55–1.94(m, 8H) | 55 | 248.9–249.3 249.3 | According to Example 1 |
| Example 14 | 206 | 9.13(br, 1H), 8.76(br-d, 1H, J=4.0Hz), 8.52(ddd, 1H, J=8.1Hz, 2.0Hz, 2.0Hz), 8.11(br-d, 1H, J=7.7Hz) 7.71 (br-s, 1H), 7.23–7.58(m, 3H), 2.44(br-t, 2H, J=7.4 Hz), 1.26–1.60(m, 26H), 0.88(br-t, 3H J=5.1Hz) | 93 | 139 | According to Example 2 |
| Example 15 | 208 | 7.82(br, 1H), 7.44(dd, 1H, J=8.1Hz, 1.5Hz), 7.33(dd, 1H, J=8.1Hz, 1.5Hz), 6.80(dd, 1H, J=8.1Hz, 8.1Hz), 2.44(t, 2H, J=7.9Hz), 1.26–1.80(m, 26H), 0.88(br, 3H) | 5 | — | According to Example 2 |
| Example 16 | 209 | 6.94–7.94(m, 4H), 2.02–2.16(m, 5H), 1.55–1.82(m, 8H), 1.25–1.37(m, 16H), 0.87(br-t, 3H, J=5.5Hz) | 72 | 48–51 | According to Example 2 |
| Example 17 | 210 | 8.19–8.28(m, 3H), 7.23–7.58(m, 5H), 2.51(t, 2H, J= 7.0Hz), 1.17–1.82(m, 26H), 0.88(br, 3H) | 54 | 137–139 | According to Example 2 |
| Example 18 | 211 | 8.02–8.28(m, 3H), 7.31–7.72(m, 6H), 2.28(br-t, 2H, J=6.8Hz), 1.66–1.85(m, 8H), 1.16–1.49(m, 18H), 0.84 (br-t, 3H, J=5.5HZ) | 51 | 99 | According to Example 2 |
| Example 19 | 212 | 8.07–8.18(m, 2H), 7.22–7.45(m, 5H), 7.25(d, 2H, J= 8.8Hz), 6.77(d, 2H, J=8.8Hz), 3.97(br, 2H), 2.37(s, 3H), 2.18(s, 3H), 1.53–1.86(m, 6H), 1.41(s, 6B), 1.28 (s, 9H) | 62 | Oily Substance | According to Example 2 |
| Example 20 | 213 | 8.09–8.20(m, 2H), 7.45–7.51(m, 4H), 7.17(s, 1H), 2.38(s, 3H), 2.21(s, 3H), 1.14–1.87(m, 26H), 0.87 (br, 3H) | 18 | Oily Substance | According to Example 2 |
| Example 21 | 306 | 7.21(s, 2H), 6.57(s, 2H), 5.85(br-s, 2H), 2.97(s, 4H), 2.16(s, 6H), 1.45(s, 12H) | 50 | 228–229 | According to Example 3 |
| Example 22 | 307 | 6.92(d, 2H, J=7.5Hz), 6.67(d, 2H, J=7.5Hz), 5.9(br-s, 2H), 2.99(s, 4H), 2.30(s, 6H), 1.47(s, 12H) | 43 | 151–159 | According to Example 3 |
| Example 23 | 308 | 6.94(d, 1H, J=8Hz), 6.69(d, 1H, J=8Hz), 5.65(br-s, 1H), 4.7(br-s, 1H), 3.1–3.35(m, 2H), 3.01(s, 2H), 2.25(s, 3H), 1.46(s, 6H), 1.1–1.6(m, 20H), 0.88(br-t, 3H, J=7Hz) | 55 | 67–68 | According to Example 3 |
| Example 24 | 310 | 6.99(s, 1H), 6.60(s, 1H), 5.64(s, 1H), 4.4(br-s, 1H), 3.2(m, 2H), 2.97(s, 2H), 2.21(s, 3H), 1.1–1.7(m, 26H), 0.88(br-t, 3H, J=7Hz) | 76 | 85–86 | According to Example 3 |
| Example 25 | 311 | 7.0–7.3(m, 5H), 6.78(s, 1H), 6.53(s, 1H), 5.55(br-s, 1H), 4.1(br-s, 1H), 3.2–3.4(m, 2H), 2.89(s, 2H), 2.10(s, 3H), 1.5–2.1(m, 8H), 1.46(s, 6H) | 83 | 192–193 | According to Example 3 |
| Example 26 | 405 | 7.86(br-d, 2H, J=6.5Hz), 6.94(br-d, 2H, J=6.5Hz) 7.25(br-s, 1H), 6.56(s, 1H), 4.00(m, 2H), 2.91(s, 2H), 2.22(s, 3H), 2.16(s, 3H), 1.8(m, 2H), 1.3–1.6 (m, 18H), 0.89(t, 3H, J=6.7Hz) | 59 | 85–88 | According to Example 5 |
| Example 27 | 406 | 7.85(d, 2H, J=8Hz), 7.22(br-s, 1H), 6.93(d, 2H, J=8 Hz), 6.55(s, 1H), 4.00(t, 2H, J=6.5Hz), 2.90(s, 2H), 2.21(s, 3H), 2.16(s, 3H), 1.1–1.9(m, 22H), 0.88(t, 3H, J=7Hz) | 99 | 97–98 | According to Example 5 |
| Example 28 | 407 | 7.85(d, 2H, J=7Hz), 7.24(br-s; 1H), 6.93(d, 2H, J=7 Hz), 6.55(s, 1H), 4.00(t, 2H, J=6.5Hz), 2.90(s, 2H), 2.22(s, 3H), 2.16(s, 3H), 1.2–1.9(m, 24H), 0.88(t, 3H, J=7Hz) | 99 | 57–60 | According to Example 5 |
| Example 29 | 409 | 7.85(br-d, 2H, J=8.3Hz), 7.26(s, 1H), 6.93(br-d, 2H, J=8.3Hz), 6.56(s, 1H), 4.01(t, 2H, J=7.4Hz), 3.4(t, 2H, J=6.5Hz), 3.37(t, 2H, J=6.8Hz), 2.91(s, 2H), 2.22(s, 3H), 2.16(s, 3H), 1.82(m, 2H), 1.4–1.7(m, 16H) | 98 | 69–71 | According to Example 5 |
| Example 30 | 410 | 7.85(br-d, 2H, J=8.8Hz), 7.20(br-s, 1H), 6.94(br-d, 2H, J=8.8Hz), 6.56(s, 1H), 4.01(t, 2H, J=6.4Hz), 3.41(t, 2H, J=6.4Hz), 3.17(d, 2H, J=6.8Hz), 2.92(s, 2H), 2.22(s, 3H), 2.16(s, 3H), 1.83(m, 3H), 1.4–1.7 (m, 14H), 0.91(d, 6H, J=6.8Hz) | 54 | 91–97 | According to Example 5 |
| Example 31 | 411 | 7.86(br-d, 2H, J=8Hz), 7.22(d, 2H, J=9Hz), 7.2(br-s, 1H), 6.93(br-d, 2H, J=8Hz), 6.81(d, 2H, J=9Hz), 6.56 (s, 1H), 4.03(t, 2H, J=6.5Hz), 3.94(t, 2H, J=6.5Hz), 2.92(s, 2H), 2.21(s, 3H), 2.16(s, 3H), 1.83(m, 4H), 1.4–1.7(m, 14H) | 86 | 135–136 | According to Example 5 |

TABLE 1-continued

| | Compound No. | $^1$H NMR Data (CDCl$_3$) δ (ppm) | Yield (%) | m.p. (°C.) | Synthetic method |
|---|---|---|---|---|---|
| Example 32 | 412 | 6.84(s, 6H), 6.58(s, 2H), 6.57(s, 1H), 3.94(t, 2H, J=6.6Hz), 2.93(s, 2H), 2.45(s, 6H), 2.34(s, 3H), 2.16(s, 3H), 1.77(m, 2H), 1.2–1.6(m, 20H), 0.88(t, 3H, J=7.1Hz) | 47 | Oily Substance | According to Example 5 |
| Example 33 | 413 | 7.76(br-d, 2H, J=8.7Hz), 7.19(br, 1H), 6.60(d, 2H, J=8.7Hz), 6.54(s, 1H), 3.16(t, 2H, J=7.2Hz), 2.91 (s, 2H), 2.21(s, 3H), 2.16(s, 3H), 1.43(s, 6H), 1.24–1.47(m, 16H), 0.89(t, 3H, J=7.2Hz) | 24 | — | According to Example 5 |
| Example 34 | 427 | 8.0(br-s, 1H), 6.75–7.3(m, 3H), 3.04(s, 2H), 2.2–2.5 (m, 2H), 1.15–1.9(m, 26H), 1.48(s, 6H), 0.88 (br-t, 3H, J=7Hz) | 90 | 90–92 | According to Example 4 |
| Example 35 | 428 | 8.0–8.15(m, 1H), 7.4(br, 1H), 6.7–6.9(m, 2H), 3.04 (s, 2H), 2.0–2.3(m, 2H), 1.0–1.9(m, 30H), 0.87 (br-t, 3H, J=7Hz) | 91 | Oily Substance | According to Example 4 |
| Example 36 | 430 | 6.89(d, 1H, J=8Hz), 6.80(br-s, 1H), 6.65(d, 1H, J= 8Hz), 2.97(s, 2H), 2.18(s, 3H), 2.0–2.35(m, 2H), 1.05–1.8(m, 30H), 0.87(br-t, 3H, J=7Hz) | 98 | 97–107 | According to Example 4 |
| Example 37 | 431 | 7.27(d, 2H, J=9.0Hz), 6.55–6.98(m, 5H), 3.95(t, 2H J=6.3Hz), 2.97(s, 2H), 2.17(s, 3H), 1.45–1.9(m, 6H), 1.41(s, 6H), 1.1–1.4(m, 15H) | 95 | 101–103 | According to Example 4 |
| Example 38 | 432 | 6.78(br-s, 1H), 6.49(s, 1H), 3.40(t, 2H, J=6.9Hz), 2.88(s, 2H), 2.13(s, 6H), 1.1–2.0(m, 10H), 1.43(s, 6H), 1.29(s, 6H) | 73 | 80–81 | According to Example 5 |
| Example 39 | 433 | 6.77(br, 1H), 6.49(s, 1H), 2.88(s, 2H), 2.13(s, 6H), 1.0–1.7(m, 26H), 0.88(br-t, 3H, J=6Hz) | 93 | 81–82 | According to Example 5 |
| Example 40 | 435 | 6.78(br-s, 1H), 6.49(s, 1H), 2.89(s, 2H), 2.13(s, 6H), 1.0–1.7(m, 34H), 0.85(br-t, 3H, J=7Hz) | 68 | 36–38 | According to Example 5 |
| Example 41 | 437 | 7.19(br, 5H), 6.77(br, 1H), 6.49(s, 1H), 2.89(s, 2H) 2.62(t, 2H, J=7.3Hz), 2.12(s, 6H), 1.43(s, 6H), 1.28 (s, 6H), 1.28–1.72(m, 6H) | 29 | 73–73.8 | According to Example 5 |
| Example 42 | 438 | 7.1–7.3(m, 5H), 6.78(br-s, 1H), 6.49(s, 1H), 2.88 (s, 2H), 2.60(t, 2H, J=8Hz), 2.13(s, 6H), 1.2–1.9 (m, 8H); 1.41(s, 6H), 1.27(s, 6H) | 78 | 69–71 | According to Example 5 |
| Example 43 | 439 | 7.1–7.4(m, 5H), 6.75(br-s, 1H), 6.48(s, 1H), 2.87 (s, 2H), 2.59(t, 2H, J=6.5Hz), 2.13(s, 6H), 1.0–1.8 (m, 10H), 1.40(s, 6H), 1.27(s, 6H) | 85 | 51–52 | According to Example 5 |
| Example 44 | 440 | 7.09(d, 2H, J=7.9Hz), 7.06(d, 2H, J=7.9Hz), 6.76 (br-s, 1H), 6.49(s, 1H), 2.87(s, 2H), 2.59(t, 2H, J= 7.5Hz), 2.54(t, 2H, J=7.5Hz), 2.13(s, 6H), 1.5–1.8 (m, 6H), 1.38(s, 6H), 1.28(s, 6H), 0.93(t, 3H, J= 7.2Hz) | 96 | 88–91 | According to Example 5 |
| Example 45 | 441 | 6.9–7.2(m, 4H), 6.75(br-s, 1H), 6.49(s, 1H), 2.87 (s, 2H), 2.2–2.7(m, 4H), 2.13(s, 6H), 1.4–1.95(m, 5H), 1.38(s, 6H), 1.28(s, 6H), 0.89(d, 6H, J=6.5Hz) | 82 | 98–100 | According to Example 5 |
| Example 46 | 442 | 7.08(d, 2H, J=8.6Hz), 6.80(d, 2H, J=8.6Hz), 6.77 (br, 1H), 6.50(s, 1H), 3.91(t, 2H, J=6.6Hz), 2.88 (s, 2H), 2.57(t, 2H, J=6.6Hz), 2.13(s, 6H), 1.2–1.8 (m, 24H), 0.90(t, 3H, J=6.9Hz) | 85 | Oily Substance | According to Example 5 |
| Example 47 | 443 | 6.8(br-s, 1H), 6.49(s, 1H), 3.25–3.55(m, 4H), 2.89 (s, 2H), 2.13(s, 6H), 1.0–1.8(m, 23H), 0.87(d, 6H, J=6, 2Hz) | 81 | Oily Substance | According to Example 5 |
| Example 48 | 444 | 6.77(br-s, 1H), 6.49(s, 1H), 3.37(t, 4H, J=6.4Hz), 2.88(s, 2H), 2.13(s, 6H), 1.0–1.8(m, 37H), 0.88(d, 6H, J=6.1Hz) | 61 | Oily Substance | According to Example 5 |
| Example 49 | 445 | 6.8(br-s, 1H), 6.49(s, 1H), 3.38(t, 2H, J=6.5Hz), 3.15(d, 2H, J=6.5Hz), 2.88(s, 2H), 2.13(s, 6H), 1.1–1.9(m, 23H), 0.89(d, 6H, J=6.5Hz) | 66 | 45–47 | According to Example 5 |
| Example 50 | 446 | 6.77(br-s, 1H), 6.49(s, 1H), 3.38(t, 2H, J=6.2Hz), 3.03(s, 2H), 2.89(s, 2H), 2.13(s, 6H), 1.1–1.75 (m, 22H), 0.89(s, 9H) | 42 | Oily Substance | According to Example 5 |
| Example 51 | 447 | 6.78(br, 1H), 6.49(s, 1H), 3.39(t, 2H, J=6.3Hz), 3.15(d, 2H, J=6.8Hz), 2.88(s, 2H), 2.13(s, 6H), 1.0–2.1(m, 21H), 0.88(d, 6H, J=6.6Hz) | 46 | Oily Substance | According to Example 5 |
| Example 52 | 448 | 6.8(br, 1H), 6.49(s, 1H), 3.3–3.6(m, 2H), 2.89(s, 2H), 2.13(s, 6H), 1.1–1.95(m, 33H) | 30 | Oily Substance | According to Example 5 |
| Example 53 | 449 | 7.2–7.4(m, 5H), 6.80(br-s, 1H), 6.49(s, 1H), 4.48 (s, 2H), 3.47(t, 2H, J=6.5Hz), 2.88(s, 2H), 2.13(s, 6H), 1.2–1.8(m, 6H), 1.41(s, 6H), 1.28(s, 6H) | 54 | 78–79 | According to Example 5 |
| Example 54 | 450 | 7.23(s, 5H), 6.8(br-s, 1H), 6.49(s, 1H), 3.61(t, 2H, J=7Hz), 3.42(t, 2H, J=7Hz), 2.7–3.0(m, 4H), 2.13(s, 6H), 1.2–1.8(m, 20H) | 31 | Oily Substance | According to Example 5 |
| Example 55 | 451 | 6.78(br, 1H), 6.49(s, 1H), 3.3–3.8(m, 3H), 3.55(s, 4H), 2.88(s, 2H), 2.13(s, 6H), 1.0–1.8(m, 26H) | 49 | Oily Substance | According to |

TABLE 1-continued

| | Compound No. | ¹H NMR Data (CDCl₃) δ (ppm) | Yield (%) | m.p. (°C.) | Synthetic method |
|---|---|---|---|---|---|
| Example 56 | 452 | 6.8(br, 1H), 6.49(s, 1H), 3.39(t, 2H, J=6Hz), 3.31 (s, 3H), 2.89(s, 2H), 2.13(s, 6H), 1.2–1.9(m, 22H) | — | Oily Substance | According to Example 5 |
| Example 57 | 453 | 7.20(d, 2H, J=9Hz), 6.85(br-s, 1H), 6.78(d, 2H, J=9Hz), 6.50(s, 1H), 3.93(t, 2H, J=6Hz), 2.89(s, 2H), 2.14(s, 6H), 1.5–1.9(m, 4H), 1.41(s, 6H), 1.33(s, 6H) | 75 | 116.5–117 | According to Example 5 |
| Example 58 | 454 | 7.27(d, 2H, J=9Hz), 6.80(d, 2H, J=9Hz), 6.49(s, 1H), 3.94(t, 2H, J=6Hz), 2.88(s, 2H), 2.13(s, 6H), 1.4–1.9(m, 6H), 1.41(s, 6H), 1.29(s, 15H) | 85 | 110–111 | According to Example 5 |
| Example 59 | 455 | 7.20(d, 2H, J=9Hz), 6.85(br-s, 1H), 6.79(d, 2H, J=9Hz), 6.50(s, 1H), 3.92(t, 2H, J=6Hz), 2.88(s, 2H), 2.16(s, 3H), 2.13(s, 3H), 1.1–1.9(m, 6H), 1.41(s, 6H), 1.31(s, 6H) | 87 | 91–92 | According to Example 5 |
| Example 60 | 456 | 7.1–7.3(m, 2H), 6.7–7.0(m, 4H), 6.49(s, 1H), 3.95, (t, 2H, J=6Hz), 2.88(s, 2H), 2.13(s, 6H), 1.3–1.95 (m, 8H), 1.42(s, 6H), 1.29(s, 6H) | 71 | 108 | According to Example 5 |
| Example 61 | 457 | 7.20(d, 2H, J=9Hz), 6.79(d, 2H, J=9Hz), 6.7(br-s, 1H), 6.49(s, 1H), 3.91(t, 2H, J=6Hz), 2.88(s, 2H), 2.13(s, 6H), 1.2–1.95(m, 8H), 1.42(s, 6H), 1.29 (s, 6H) | 83 | 90–91 | According to Example 5 |
| Example 62 | 458 | 7.06(d, 2H, J=8.5Hz), 6.76(d, 2H, J=8.5Hz), 6.8(br-s, 1H), 6.49(s, 1H), 3.92(t, 2H, J=6.5Hz), 2.88(s, 2H), 2.27(s, 3H), 2.13(s, 6H), 1.2–1.95(m, 8H), 1.42(s, 6H), 1.29(s, 6H) | 87 | 102–104 | According to Example 5 |
| Example 63 | 459 | 7.05–7.4(m, 2H), 6.7–6.9(m, 2H), 6.49(s, 1H), 3.98 (t, 2H, J=6Hz), 2.88(s, 2H), 2.13(s, 6H), 1.2–1.95 (m, 8H), 1.42(s, 6H), 1.30(s, 6H) | 82 | 88–89 | According to Example 10 |
| Example 64 | 460 | 6.5–7.05(m, 4H), 6.49(s, 1H), 3.92(t, 2H, J=6Hz), 2.88(s, 2H), 2.24(s, 3H), 2.17(s, 3H), 2.13(s, 6H), 1.1–1.95(m, 8H), 1.42(s, 6H), 1.29(s, 6H) | 77 | 100–102 | According to Example 10 |
| Example 65 | 461 | 7.12(d, 2H, J=9Hz), 6.85(br-s, 1H), 6.80(d, 2H, J=9Hz), 6.49(s, 1H), 3.92(t, 2H, J=6Hz), 2.89(s, 2H), 2.13(s, 6H), 1.0–2.0(m, 27H) | 43 | 118–120 | According to Example 10 |
| Example 66 | 463 | 6.5–6.9(m, 5H), 6.49(s, 1H), 3.87(t, 2H, J=6Hz), 2.88(s, 2H), 2.13(s, 6H), 1.2–2.0(m, 8H), 1.42(s, 6H), 1.29(s, 6H) | 91 | 100–105 | According to Example 7 |
| Example 67 | 464 | 6.7–6.95(m, 5H), 6.49(s, 1H), 3.89(t, 2H, J=6Hz), 2.88(s, 2H), 2.85(s, 6H), 2.13(s, 6H), 1.2–1.9(m, 8H), 1.42(s, 6H), 1.28(s, 6H) | 60 | 108–108.5 | According to Example 8 |
| Example 68 | 465 | 7.19(d, 2H, J=6.9Hz), 6.8(br-s, 1H), 6.79(d, 2H, J=6.9Hz), 6.49(s, 1H), 3.90(t, 2H, J=6.5Hz), 2.88 (s, 2H), 2.13(s, 6H), 1.3–1.9(m, 10H), 1.42(s, 6H), 1.29(s, 6H) | 85 | 79–80 | According to Example 5 |
| Example 69 | 466 | 7.16(d, 2H, J=8Hz), 6.85(br-s, 1H), 6.77(d, 2H, J=8Hz), 6.49(s, 1H), 3.91(t, 2H, J=6Hz), 2.88(s, 1H), 2.27(s, 3H), 2.13(s, 6H), 1.2–1.9(m, 10H), 1.42(s, 6H), 1.28(s, 6H) | 38 | 79–80 | According to Example 5 |
| Example 70 | 467 | 6.7–7.1(m, 5H), 6.49(s, 1H), 3.89(t, 2H, J=6Hz), 2.88(s, 2H), 2.13(s, 6H), 1.2–1.9(m, 10H), 1.42(s, 6H), 1.28(s, 6H) | 55 | 71–72 | According to Example 10 |
| Example 71 | 468 | 6.6–6.9(m, 5H), 6.49(s, 1H), 3.89(t, 2H, J=6Hz), 2.88 (s, 2H), 2.85(s, 6H), 2.13(s, 6H), 1.2–1.9(m, 10H), 1.43(s, 6H), 1.28(s, 6H) | 64 | Oily Substance | According to Example 8 |
| Example 72 | 470 | (Free)6.79(br, 1H), 6.48(s, 1H), 3.44(br, 1H), 2.88(s, 2H), 2.60(t, 2H, J=6.8Hz), 2.12(s, 6H), 1.43 (s, 6H), 1.27(s, 6H), 1.27–1.69(m, 10H), 1.17(s, 9H) | 36 (HCl salt) | 146–149 (HCl salt) | According to Example 11 |
| Example 73 | 471 | (Free)7.25(br-s, 4H), 6.78(s, 1H), 6.48(s, 1H), 3.73(s, 2H), 2.88(s, 2H), 2.58(t, 2H, J=7.0Hz), 2.12 (s, 6H), 1.42(s, 6H), 1.27(s, 6H), 1.27–1.64(m, 10H) | 10 (HCl salt) | 191–193 (HCl salt) | According to Example 11 |
| Example 74 | 472 | (Free)7.28(br, 5H), 6.79(br, 1H), 6.48(s, 1H), 3.50(s, 2H), 2.87(s, 2H), 2.38(t, 2H, J=6.2Hz), 2.19 (s, 3H), 2.12(s, 6H), 1.41(s, 6H), 1.27(s, 6H), 1.27–1.65(m-10H) | 79 (HCl salt) | Amorphous | According to Example 11 |
| Example 75 | 473 | 7.27(d, 2H, J=8.8Hz), 7.17(d, 2H, J=8.8Hz), 6.78 (br, 1H), 6.48(s, 1H), 4.41(s, 2H), 4.10(t, 2H, J=6.6Hz), 2.88(s, 2H), 2.83(s, 3H), 2.13(s, 6H), 1.41 (s, 6H), 1.28(s, 6H), 1.27–1.72(m, 10H) | 28 | Oily Substance | According to Example 11 |
| Example 76 | 474 | (Free)6.86(br, 1H), 6.48(s, 1H), 2.88(s, 2H), 2.32-2.56(m, 6H), 2.12(s, 6H), 1.43(s, 6H), 1.27(s, 6H), 1.27–1.65(m, 16H) | 26 (HCl salt) | 177–180 (HCl salt) | According to Example 5 |
| Example 77 | 475 | (Free)6.80(br, 1H), 6.48(s, 1H), 2.88(s, 2H), 2.47(br, 10H), 2.28(s, 3H), 2.13(s, 6H), 1.43(s, 6H), 1.27(s, 6H), 1.27–1.60(m, 10H) | 28 (HCl salt) | 175–178 (HCl salt) | According to Example 5 |
| Example | 476 | 7.28(br, 5H), 6.88(br, 1H), 6.49(s, 1H), 3.47(s, | 22 | 100–101 | According |

TABLE 1-continued

| | Compound No. | $^1$H NMR Data (CDCl$_3$) δ (ppm) | Yield (%) | m.p. (°C.) | Synthetic method |
|---|---|---|---|---|---|
| 78 | | 2H), 2.89(s, 2H), 2.27–2.49(m, 10H), 2.13(s, 6H), 1.42(s, 6H), 1.28(s, 6H), 1.28–1.69(m, 6H) | | | to Example 5 |
| Example 79 | 477 | 7.28(br, 5H), 6.76(br, 1H), 6.48(s, 1H), 3.49(s, 2H), 2.87(s, 2H), 2.22–2.46(m, 10H), 2.12(s, 6H), 1.42(s, 6H), 1.26(s, 6H), 1.26–1.56(m, 10H) | 55 | Oily Substance | According to Example 5 |
| Example 80 | 478 | 7.86(br-d, 2H, J=8.5Hz), 7.26(br-s, 1H), 6.94(br-d, 2H, J=8.5Hz), 6.56(s, 1H), 4.01(t, 2H, J=6.6Hz), 2.91(s, 2H), 2.22(s, 3H), 2.16(s, 3H), 1.83(m, 2H), 1.2–1.6(m, 26H), 0.89(t, 3H, J=7.5Hz) | 81 | 97 | According to Example 5 |
| Example 81 | 480 | 6.6(br-s, 1H), 6.51(s, 1H), 2.90(s, 3H), 2.1–2.5(m, 2H), 2.16(s, 6H), 1.5–1.8(m, 2H), 1.45(s, 6H), 1.1–1.5(m, 24H), 0.88(br-t, 3H, J=7Hz) | 89 | 84–85.5 | According to Example 5 |
| Example 82 | 481 | 6.73(br-s, 1H), 6.49(s, 1H), 2.89(s, 2H), 2.0–2.45 (m, 2H), 2.13(s, 6H), 1.1–1.85(m, 30H), 0.87(br-t, 3H, J=7Hz) | 73 | 65–66 | According to Example 5 |
| Example 83 | 482 | 6.5(br-s, 1H), 2.96(s, 2H), 2.1–2.5(m, 2H), 2.22(s, 6H), 1.55–1.9(m, 2H), 1.50(s, 3H), 1.45(s, 3H), 1.05–1.4(m, 24H), 0.87(br-t, 3H, J=7Hz) | 65 | 114–115 | According to Example 4 |
| Example 84 | 483 | 6.78(br, 1H), 2.95(s, 2H), 2.0–2.35(m, 2H), 2.20 (s, 6H), 1.1–1.8(m, 30H), 0.88(br-t, 3H, J=7Hz) | 87 | 69–70 | According to Example 4 |
| Example 85 | 521 | 7.36(s, 1H), 6.77(br, 1H), 6.55(s, 1H), 2.97(s, 2H), 2.0–2.5(m, 2H), 2.17(s, 2H), 2.5–2.8(m, 2H), 1.45 (s, 6H), 1.05–1.55(m, 24H), 0.88(br-t, 3H, J=7Hz) | 86 | 85–87 | According to Example 4 |
| Example 86 | 522 | 7.42(s, 1H), 6.94(br-s, 1H), 6.54(s, 1H), 2.96(s, 2H), 2.0–2.5(m, 5H), 1.1–1.9(m, 30H), 0.87(br-t, 3H, J=7Hz) | 70 | 66 | According to Example 4 |

EXAMPLE 87

Synthesis of N-(2,2,4,6-tetramethyl-2,3-dihydrobenzofuran-7-yl)-4-(4-chlorobenzyloxy)benzoylamide (408)

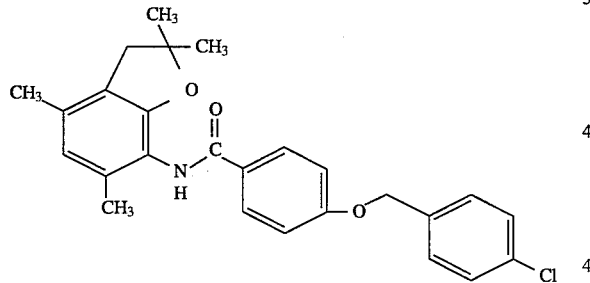

A 62 mg amount of N-(2,2,4,6-tetramethyldihydro-1-benzofuran-7-yl)-4-hydroxybenzoylamide was dissolved in 2 ml of acetonitrile. A 38 mg amount of 4-chlorobenzyl chloride and 41 mg of potassium carbonate were added thereto, and the mixture was allowed to react under reflux for 10 hrs.

After the completion of the reaction, potassium carbonate was removed, the residue was concentrated by removing the solvent, and the concentrate was purified by preparative thin-layer chromatography (hexane:ethyl acetate=4:6) to provide 72 mg of the title compound.

Property values $^1$H NMR (CDCl$_3$) δ (ppm): 7.89 (br, 2H), 7.37 (s, 4H), 7.25 (br, 1H), 7.01 (br-d, J=8.7Hz, 2H), 6.56(s, 1H), 2.92(s, 2H), 2.21(s, 3H), 2.16(s, 3H), 1.44(s, 6H) m.p.: 148°–150° C.

EXAMPLE 88

Synthesis of N-(2,2,4,6-tetramethyl-2,3-dihydrobenzofuran-7-yl)3-(4-decyloxyphenyl)-3-oxpropaneamide (479)

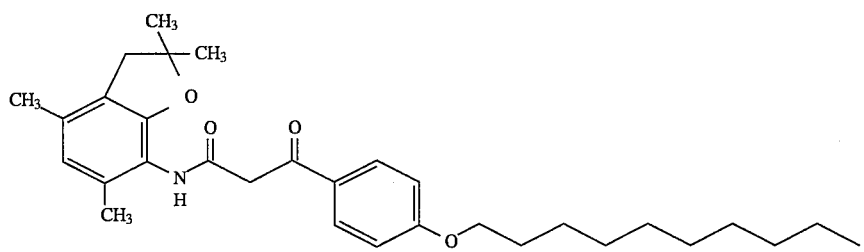

A 1.36 ml amount of a 1.6M n-butyl lithium hexane solution was added by portions to a solution of 304 µl of diisopropylamine in 5 ml of dry tetrahydrofuran at −78° C., and the mixture was stirred at that temperature for 30 min. Subsequently, a solution of 500 mg of 4-decyloxyacetophenone in 5 ml of dry tetrahydrofuran was added at 0° C., and the mixture was stirred at that temperature for 15 min and then at room temperature for one hour.

Separately, 2,2,4,6-tetramethyl-2,3-dihydrobenzofuran-7-yl isocyanate was prepared from 412 mg of 2,2,4,6-tetramethyl-7-aminodihydro-1-benzofuran according to the reference examples. The above-described stirred solution was added to a solution of the 2,2,4,6-tetramethyl-2,3-dihydrobenzofuran-7-yl isocyanate in 5 ml of dry tetrahydrofuran at room temperature.

The mixture was allowed to react for 15 hrs. An aqueous potassium hydrogensulfate was added to the reaction mixture, and the mixture was extracted with ethyl acetate.

The extract was concentrated by removing the organic solvent, and the concentrate was purified by silica gel column chromatography (hexane:ethyl acetate= 6:4). The product was further recrystallized from hexane to provide 440 mg of the title compound.

Property values $^1$H NMR (CDCl$_3$) δ (ppm): 8.31 (br, 1H), 8.02 (d, J=8.9Hz, 2H), 6.95 (d, J=8.9Hz, 2H), 6.50(s, 1H), 4.09(s, 2H), 4.03(t, J=6.6Hz, 2H), 2.89(s, 2H), 2.13(s, 3H), 2.11(s, 3H), 1.81(tt, J=6.6Hz, J=6.9Hz, 2H), 1.28–1.55(m, 14H), 0.88 (t, J=6.6Hz, 3H) m.p.: 118.5°–119° C.

EXAMPLE 89

Synthesis of N-(5-dodecaneamide-2,2,4,6-tetramethyl-2,3-dihydrobenzofuran-7-yl)-2,2-dimethyldodecaneamide (535)

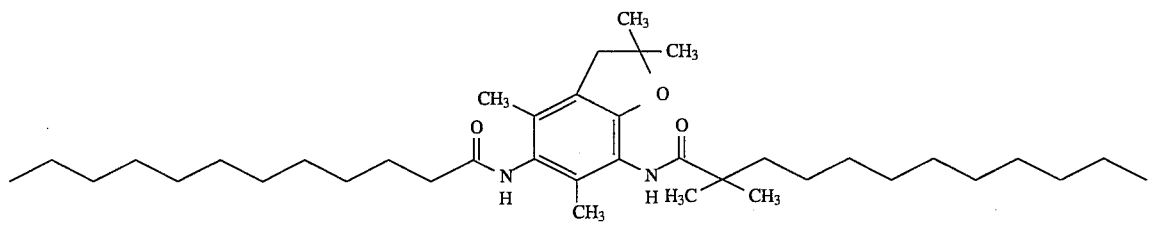

A 42 mg amount of N-(5-amino-2,2,4,6-tetramethyl-2,3-dihydrobenzofuran-7-yl)-2,2-dimethyldodecaneamide (486) was dissolved in 2.0 ml of dichloromethane, and 13 mg of triethylamine was added thereto. Further, 22 mg of n-dodecanoyl chloride was added thereto, and the mixture was allowed to react at room temperature with stirring for 5 hr. The reaction solution was poured into 20 ml of water, and the mixture was extracted with ethyl acetate (10 ml×three times). The organic layer was washed with water and brine in that order and dehydrated over anhydrous magnesium sulfate, and the solvent was removed by distillation. The resultant crystal was purified by silica gel column chromatography to provide 40 mg of the intended title compound. The yield was 67.6%.

$^1$H NMR (CDCl$_3$) δ (ppm): 6.86(br-s, 1H), 6.70(br-s, 1H), 2.92(s, 2H), 2.39(t, 2H, J=7.9Hz), 2.02(s, 3H), 2.00(s, 3H), 1.56(br-t, 4H, J=6Hz), 1.1–1.5(m, 32H), 0.88(t, 6H, J=7.6Hz)

EXAMPLE 90

Measurement of ACAT enzyme inhibitory activity (measurement of ACAT enzyme inhibitory activity of rabbit intestinal mucosa)

Preparation of a domestic rabbit intestinal mucosa microsome and measurement of the ACAT enzyme activity were conducted by slightly modifying a method established by Salone and Field (see Biochemica et Biophysica, vol. 712, 557 (1982).

The domestic rabbit intestinal mucosa was homogenized by using a 40 mM phosphate buffer having a pH value of 7.4 (buffer A) containing 30 mM EDTA, 50 mM KCl and 0.1M sucrose and centrifuged at 10,000×g and a temperature of 4° C. for 30 min to provide a supernatant. The supernatant was further centrifuged at 105,000×g and a temperature of 4° C. for one hour to provide a precipitate. The precipitate was resuspended in the buffer A to provide a microsome fraction.

A 1 %v/v dimethylsulfoxide solution of each specimen compound in a predetermined concentration was added to the buffer A containing 43 µM serum albumin and 0.5 mg/ml microsome fraction, and the mixture was heated at 37° C. for 5 min.

Then, 43 µM oleoyl CoA containing [1$^{-14}$C] oleoyl CoA (3.7 kB) was added thereto, the mixture was heated at 37° C. for 10 rain, and chloroform/methanol (2/1) containing 10 mg/ml cholesteryl oleate was added thereto to terminate the reaction.

0.111 kB of [$^3$H] cholesteryl oleate and 1N hydrochloric acid were added thereto, and the mixture was stirred. The cholesteryl oleate extracted into the chloroform layer was isolated by thin-layer chromatography, and the radioactivity was measured as the ACAT activity. The results are given in Table 2.

TABLE 2

| Test Compound | ACAT Inhibitory Activity, IC$_{50}$ (M) |
|---|---|
| Compound of Ex. 2 | 8.3 × 10$^{-7}$ |
| Compound of Ex. 3 | 3.4 × 10$^{-7}$ |
| Compound of Ex. 4 | 2.4 × 10$^{-8}$ |
| Compound of Ex. 5 | 4.2 × 10$^{-8}$ |
| Compound of Ex. 6 | 1.9 × 10$^{-8}$ |
| Compound of Ex. 8 | 2.0 × 10$^{-8}$ |
| Compound of Ex. 10 | 2.3 × 10$^{-7}$ |
| Compound of Ex. 13 | 4.0 × 10$^{-7}$ |
| Compound of Ex. 18 | 5.0 × 10$^{-7}$ |
| Compound of Ex. 23 | 2.2 × 10$^{-7}$ |
| Compound of Ex. 27 | 3.0 × 10$^{-8}$ |
| Compound of Ex. 28 | 9.0 × 10$^{-8}$ |
| Compound of Ex. 33 | 1.1 × 10$^{-7}$ |
| Compound of Ex. 34 | 8.9 × 10$^{-7}$ |
| Compound of Ex. 35 | 5.0 × 10$^{-7}$ |
| Compound of Ex. 36 | 2.4 × 10$^{-7}$ |
| Compound of Ex. 37 | 3.4 × 10$^{-7}$ |
| Compound of Ex. 38 | 1.8 × 10$^{-7}$ |
| Compound of Ex. 39 | 7.2 × 10$^{-8}$ |
| Compound of Ex. 40 | 3.3 × 10$^{-8}$ |
| Compound of Ex. 41 | 2.1 × 10$^{-7}$ |
| Compound of Ex. 42 | 1.2 × 10$^{-7}$ |
| Compound of Ex. 43 | 8.1 × 10$^{-8}$ |
| Compound of Ex. 44 | 6.6 × 10$^{-8}$ |
| Compound of Ex. 45 | 2.8 × 10$^{-8}$ |
| Compound of Ex. 46 | 3.4 × 10$^{-8}$ |
| Compound of Ex. 47 | 1.9 × 10$^{-7}$ |
| Compound of Ex. 48 | 5.7 × 10$^{-8}$ |
| Compound of Ex. 49 | 5.9 × 10$^{-8}$ |
| Compound of Ex. 50 | 4.5 × 10$^{-8}$ |
| Compound of Ex. 51 | 8.2 × 10$^{-8}$ |
| Compound of Ex. 52 | 4.2 × 10$^{-8}$ |
| Compound of Ex. 53 | 4.0 × 10$^{-7}$ |
| Compound of Ex. 54 | 1.0 × 10$^{-7}$ |
| Compound of Ex. 55 | 1.7 × 10$^{-7}$ |
| Compound of Ex. 56 | 3.3 × 10$^{-7}$ |
| Compound of Ex. 57 | 2.6 × 10$^{-7}$ |
| Compound of Ex. 58 | 1.7 × 10$^{-7}$ |
| Compound of Ex. 59 | 3.3 × 10$^{-7}$ |
| Compound of Ex. 60 | 8.6 × 10$^{-8}$ |
| Compound of Ex. 61 | 1.5 × 10$^{-7}$ |
| Compound of Ex. 62 | 6.4 × 10$^{-8}$ |
| Compound of Ex. 63 | 2.2 × 10$^{-7}$ |
| Compound of Ex. 64 | 9.1 × 10$^{-7}$ |
| Compound of Ex. 65 | 8.6 × 10$^{-8}$ |
| Compound of Ex. 66 | 4.6 × 10$^{-7}$ |
| Compound of Ex. 67 | 1.9 × 10$^{-7}$ |
| Compound of Ex. 68 | 7.6 × 10$^{-8}$ |
| Compound of Ex. 69 | 5.0 × 10$^{-8}$ |
| Compound of Ex. 70 | 1.1 × 10$^{-7}$ |
| Compound of Ex. 71 | 1.3 × 10$^{-7}$ |
| Compound of Ex. 73 | (HCl salt) 3.4 × 10$^{-7}$ |
| Compound of Ex. 74 | (HCl salt) 3.3 × 10$^{-7}$ |
| Compound of Ex. 75 | 1.2 × 10$^{-7}$ |
| Compound of Ex. 78 | 3.3 × 10$^{-7}$ |
| Compound of Ex. 79 | 3.5 × 10$^{-7}$ |
| Compound of Ex. 80 | 4.0 × 10$^{-8}$ |
| Compound of Ex. 81 | 2.6 × 10$^{-7}$ |
| Compound of Ex. 82 | 1.7 × 10$^{-7}$ |
| compound of Ex. 83 | 7.2 × 10$^{-8}$ |
| Compound of Ex. 84 | 2.9 × 10$^{-7}$ |
| Compound of Ex. 88 | 1.1 × 10$^{-7}$ |
| Compound of Ex. 9 in Japanese Unexamined Patent Publication (Kokai) No. 63-253060 | 1.4 × 10$^{-7}$ |

All the test compounds had a LD$_{50}$ value of 2 g/kg or more (mouse).

EXAMPLE 91

Measurement of percentage change of serum cholesterol

Male Wistar rats having a weight of 200 g were preliminarily bred for 7 days while they freely ingested a normal feed (CE-2 manufactured by CLEA Japan Inc.).

Thereafter, they were bred for 3 days while they freely ingested a feed enriched with cholesterol and fat (2% cholesterol, 1% cholic acid, 20% casein, 45% fine granulated sugar, 12% coconut oil, 4% KC flock, 1% mixed vitamin, 7% mixed mineral and 8% dried fish powder; a product of CLEA Japan Inc.). During the cholesterol loading period, the test compound of the present invention was orally administered to the above test animals at a dose of 0.1 to 10 mg per kg of the weight once a day for three days. On the other hand, the excipient alone was administered to the control animals.

After 8 hrs from the last administration, the test animals were fasted. 16 hr after the initiation of the fasting, these test animals were slaughtered. The serum cholesterol level was measured for each animal.

The results were compared with those of the control and are given as percentage serum cholesterol (%) in Table 3.

Percentage change of serum cholesterol (%) = {(A−B)/B}×100 wherein A represents the total cholesterol level of serum in the group of rats to which the test compound was administered; and B represents the total cholesterol level of serum in the control group of rats.

TABLE 3

| Test Compound | Dose in Oral Administration (mg/kg) | Percentage Change of Serum Cholesterol (%) |
|---|---|---|
| Compound of Ex. 5 | 1 | −61 |
| Compound of Ex. 8 | 1 | −71 |
| Compound of Ex. 20 | 10 | −46 |
| Compound of Ex. 29 | 1 | −23 |
| Compound of Ex. 36 | 10 | −52 |
| Compound of Ex. 42 | 1 | −44 |
| Compound of Ex. 45 | 1 | −58 |
| Compound of Ex. 49 | 1 | −50 |
| Compound of Ex. 50 | 10 | −54 |
| Compound of Ex. 53 | 10 | −50 |
| Compound of Ex. 58 | 10 | −27 |
| Compound of Ex. 59 | 1 | −43 |
| Compound of Ex. 61 | 1 | −64 |
| Compound of Ex. 62 | 1 | −18 |
| Compound of Ex. 68 | 1 | −75 |
| Compound of Ex. 71 | 1 | −49 |
| Compound of Ex. 78 | 10 | −43 |
| Compound of Ex. 94 | 3 | −55 |

EXAMPLE 92

Preparation of Tablet

A tablet containing 30 mg of the compound of Example 5 was prepared according to the following formulation.

| Compound Ex. 5 | 30 mg |
|---|---|
| Lactose | 87 mg |
| Starch | 30 mg |
| Magnesium stearate | 3 mg |

Utilization in Industry

The present invention provides a pharmaceutical composition for use as an ACAT inhibitor and treating hyperlipidemia and atherosclerosis, which pharmaceutical composition contains a benzoxazole compound and a 2,3-dihydrobenzofuran compound. Further, it provides novel benzoxazole and 2,3-dihydrobenzofuran compounds which can be particularly usefully used in the above-described pharmaceutical composition.

We claim:

1. A 2,3-dihydrobenzofurane compound represented by the following formula (Ia-2) or its pharmaceutically acceptable salt:

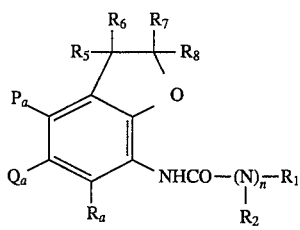

(Ia-2)

wherein $P_a$, $Q_a$ and $R_a$ each independently stands for a hydrogen atom, a halogen atom, an amino, nitro, cyano, carboxyl or hydroxyl group, a $C_1$–$C_{20}$ alkyl, $C_1$–$C_{20}$ alkoxy, $C_1$–$C_{20}$ alkanoylamino, $C_1$–$C_{20}$ monoalkylamino, $C_1$–$C_{20}$ alkyloxycarbonyl, $C_1$–$C_{20}$ alkanoyl or $C_1$–$C_{20}$ alkanoyloxy group, or a $C_2$–$C_{26}$ dialkylamino group, provided that, two or more of $P_a$, $Q_a$ and $R_a$ are not halogen atoms at the same time; and the alkyl portion of said groups may be interrupted by:

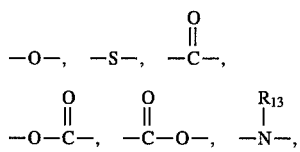

phenylene or phenyleneoxy, wherein $R_{13}$ stands for a hydrogen atom, a lower alkyl, or lower alkanoyl group, or 1 to 3 hydrogen atoms on the carbon atoms of the alkyl portion may be substituted with a phenyl group or phenyloxy group, a halogen atom or a cyano group, and the phenyl portion as the substituent may be substituted with a halogen atom, an amino, nitro, cyano, carboxyl or hydroxyl group, a $C_1$–$C_{20}$ alkyl, $C_1$–$C_{20}$ alkoxy, $C_1$–$C_{20}$ monoalkylamino, $C_1$–$C_{20}$ alkanoylamino, $C_1$–$C_{20}$ alkyloxycarbonyl, $C_1$–$C_{20}$ alkanoyl or $C_1$–$C_{20}$ alkanoyloxy group, or a $C_2$–$C_{26}$ dialkylamino group; and $R_1$ stands for a group selected from the group consisting of:

(i) an unsubstituted $C_5$–$C_7$ cycloalkyl or $C_6$ cycloalkenyl group or a $C_5$–$C_7$ cycloalkyl or $C_6$ cycloalkenyl group substituted at a position other than the 1-position with a substituent being a $C_1$–$C_{14}$ alkyl, $C_1$–$C_{14}$ alkoxy, $C_1$–$C_{14}$ alkanoylamino, $C_1$–$C_{14}$ monoalkylamino, $C_1$–$C_{14}$ alkyloxycarbonyl, $C_1$–$C_{14}$ alkanoyl or $C_1$–$C_{14}$ alkanoyloxy group or a $C_2$–$C_{26}$ dialkylamino group;

(ii) a group represented by the formula:

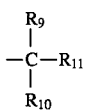

wherein $R_9$ and $R_{10}$ each independently stands for a hydrogen atom or a lower alkyl group, or may combine with each other to form a $C_3$–$C_7$ carbon ring; and $R_{11}$ stands for a substituted or unsubstituted $C_1$–$C_{19}$ alkyl, $C_2$–$C_{19}$ alkenyl, $C_6$ to $C_{10}$ aryl, $C_7$–$C_{19}$ arylalkyl, $C_1$–$C_{19}$ alkanoyl or $C_1$–$C_{19}$ alkanoyl group having a $C_4$–$C_{19}$ aromatic ring, provided that the substituent when said groups are substituted by a halogen atom, an amino, nitro, cyano, carboxyl or hydroxyl group, a $C_1$–$C_{16}$ alkyl, $C_1$–$C_{16}$ alkoxy, $C_1$–$C_{16}$ alkanoylamino, $C_1$–$C_{16}$ monoalkylamino, $C_1$–$C_{16}$ alkyloxycarbonyl, $C_1$–$C_{16}$ alkyanoyl or $C_1$–$C_{16}$ alkanoyloxy group, or a $C_2$–$C_{26}$ dialkylamino group; or $R_{11}$ stands for a group represented by the formula:

wherein A stands for a $C_1$–$C_{12}$ alkylene chain;

X stands for an oxygen atom, a sulfur atom, or a group represented by the formula:

wherein $R_{12}$ stands for a hydrogen atom or a lower alkyl or lower alkanoyl group; and B stands for a substituted or unsubstituted $C_1$–$C_8$ alkyl, $C_6$ or $C_{10}$ aryl or $C_7$–$C_8$ arylalkyl group, provided that the substituent when said groups are substituted is a halogen atom, an amino, nitro, cyano, carboxyl or hydroxyl group, a $C_1$–$C_{12}$ alkyl, $C_1$–$C_{12}$ alkoxy, $C_1$–$C_{12}$ monoalkylamino, $C_1$–$C_{12}$ alkanoylamino, $C_1$–$C_{12}$ alkyloxycarbonyl, $C_1$–$C_{12}$ alkanoyl acyl or $C_1$–$C_1$ alkanoxyloxy group, or a $C_2$–$C_{20}$ dialkylamino group; and (iii) a substituted or unsubstituted phenyl group or a group represented by the formula:

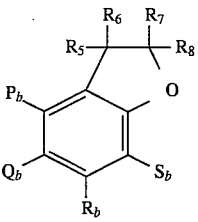

wherein any one of $P_b$, $Q_b$, $R_b$ and $S_b$ represents a bond with the remaining three substituents independently standing for a group represented by the formula —$R_3$, provided that, when the phenyl group is substituted, the substituent is present at the m- or p-position and the substituent is an amino, cyano, carboxyl or hydroxyl group, $C_1$–$C_{16}$ alkoxy, $C_1$–$C_{16}$ monoalkylamino, $C_1$–$C_{16}$ alkanoylamino, $C_1$–$C_{16}$ alkyloxycarbonyl, $C_1$–$C_{16}$ alkanoyl or $C_1$–$C_{16}$ alkanoyloxy groups, or a $C_2$–$C_{26}$ dialkylamino group; and the alkyl portion of said groups may be interrupted by:

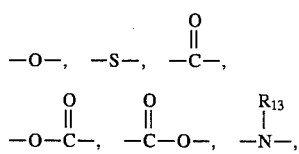

phenylene or phenyleneoxy, wherein $R_{13}$ stands for a hydrogen atom, a lower alkyl, or lower alkanoyl group, or 1 to 3 hydrogen atoms on the carbon atoms of the alkyl portion may be substituted with a phenyl or phenyloxy group, a halogen atom or a cyano group, or the phenyl portion as the substituent may be substituted with a halogen atom, an amino, nitro, cyano, carboxyl or hydroxyl group or a lower alkyl, lower alkoxy, lower monoalkylamino, lower dialkylamino, lower alkanoylamino, lower alkyloxycarbonyl, lower alkanoyl or lower alkanoyloxy group;

$R_2$ stands for a hydrogen atom or a $C_1$–$C_8$ alkyl group;

each $R_3$ independently stands for a hydrogen atom, a halogen atom, an amino, nitro, cyano, carboxyl or hydroxyl group, $C_1$–$C_{20}$ alkyl, $C_1$–$C_{20}$ alkoxy, $C_1$–$C_{20}$ monoalkylamino, $C_1$–$C_{20}$ alkanoylamino, $C_1$–$C_{20}$ alkyloxycarbonyl, $C_1$–$C_{20}$ alkanoyl or $C_1$–$C_{20}$ alkanoyloxy group, or a dialkylamino group, provided that, two or more of each $R_3$ are not halogen atoms at the same time; and $R_5$, $R_6$, $R_7$ and $R_8$ each independently stands for a hydrogen atom or a $C_1$–$C_{20}$ alkyl group, or $R_5$ and $R_6$ or $R_7$ and $R_8$ combine with a carbon atom bonded thereto to form a $C_5$–$C_7$ carbon ring; and n is 0 or 1, provided that when any one of $P_a$, $O_a$ and $R_a$ stands for an alkanoylamino group and $R_1$ stands for:

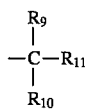

wherein $R_{11}$ represents the unsubstituted or substituted $C_1$–$C_{19}$ alkyl group, both of the alkyl group of the alkanoylamino group and the alkyl group $R_{11}$ do not have carbon atoms of $C_6$ or less at the same time.

2. A compound and its pharmaceutically acceptable salt according to claim 1, wherein the n value is 1.

3. A compound and its pharmaceutically acceptable salt according to claim 2, wherein the $R_2$ stands for a hydrogen atom.

4. A compound and its pharmaceutically acceptable salt according to claim 1, wherein the n value is 0 (zero).

5. A compound and its pharmaceutically acceptable salt according to claim 4, wherein the $R_a$ stands for a group other than a hydrogen atom.

6. A compound and its pharmaceutically acceptable salt according to claim 5, wherein the $R_1$ stands for a group represented by the formula:

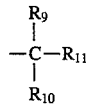

wherein the $R_9$, $R_{10}$ and $R_{11}$ are as defined above.

7. A method for treating hypercholesterolemia comprising administering, to a patient in need of such treatment, a treatment effective amount of the pharmaceutical composition comprising a 2,3-dihydrobenzofurane compound represented by the following formula (I-2) or its pharmaceutically acceptable salt:

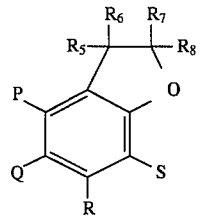

wherein any one of the P, Q, R and S is a group represented by the formula:

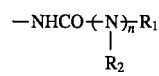

with the remaining three substituents being independently a group represented by —$R_3$, wherein $R_1$ stands for a group selected from the group consisting of:

(i) an unsubstituted $C_5$–$C_7$ cycloalkyl or $C_6$ cycloalkenyl group or a $C_5$–$C_7$ cycloalkyl or $C_6$ cycloalkenyl group substituted at a position other than the 1-position with the substituent being a $C_1$–$C_{14}$ alkyl, $C_1$–$C_{14}$ alkoxy, $C_1$–$C_{14}$ alkanoylamino, $C_1$–$C_{14}$ monoalkylamino, $C_1$–$C_{14}$ alkyloxycarbonyl, $C_1$–$C_{14}$ alkanoyl or $C_1$–$C_{14}$ alkanoyloxy group or a $C_2$–$C_{26}$ dialkylamino group;

(ii) a group represented by the formula:

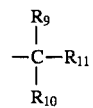

wherein $R_9$ and $R_{10}$ each independently stands for a hydrogen atom or a lower alkyl group, or may combine with each other to form a $C_3$–$C_7$ carbon ring; and $R_{11}$ stands for a substituted or unsubstituted $C_1$–$C_{19}$ alkyl, $C_2$–$C_{19}$ alkenyl, $C_6$ or $C_{10}$ aryl, $C_7$–$C_{19}$ arylalkyl, $C_1$–$C_{19}$ alkanoyl or $C_1$–$C_{19}$ alkanoyl group having a $C_4$–$C_{19}$ aromatic ring, provided that the substituent, when said groups are substituted, is a halogen atom, an amino, nitro, cyano, carboxyl or hydroxyl group, a $C_1$–$C_{16}$ monoalkylamino, $C_1$–$C_{16}$ alkyloxycarbonyl, $C_1$–$C_{16}$ alkanoyl or $C_1$–$C_{16}$ alkanoyloxy group, or a $C_2$–$C_{26}$ dialkylamino group; or $R_{11}$ stands for a group represented by the formula:

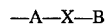

wherein A stands for a $C_1$–$C_{12}$ alkylene chain;

X stands for an oxygen atom, a sulfur atom, or a group represented by the formula:

wherein $R_{12}$ stands for a hydrogen atom or a lower alkyl or lower alkanoyl group; and B stands for a substituted or unsubstituted $C_1$–$C_8$ alkyl, $C_6$ or $C_{10}$ aryl or $C_7$–$C_8$ arylalkyl group, provided that the substituent, when said groups are substituted, is a halogen atom, an amino, nitro, cyano, carboxyl or hydroxyl group, a $C_1$–$C_{12}$ alkyl, $C_1$–$C_{12}$ alkoxy, $C_1$–$C_{12}$ monoalkylamino, $C_1$–$C_{12}$ alkanoylamino, $C_1$–$C_{12}$ alkyloxycarbonyl, $C_1$–$C_{12}$ alkanoyl acyl or $C_1$–$C_{12}$ alkanoyloxy group, or a $C_2$–$C_{20}$ dialkylamino group; and (iii) a substituted or unsubstituted phenyl group or a group represented by the formula:

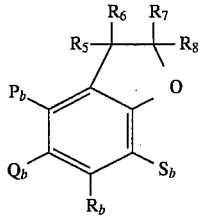

wherein any one of $P_b$, $Q_b$, $R_b$ and $S_b$ represents a bond with the remaining three substituents independently standing for a group represented by —$R_3$, provided that, when the phenyl group is substituted, the substituent is present at the o-, m- or p-position and the substituent is a halogen atom, an amino, nitro, cyano, carboxyl or hydroxyl group, a $C_1$–$C_{16}$ alkyl, $C_1$–$C_{16}$ alkoxy, $C_1$–$C_{16}$ monoalkylamino, $C_1$–$C_{16}$ alkanoylamino, $C_1$–$C_{16}$ alkyloxycarbonyl, $C_1$–$C_{16}$ alkanoyl or $C_1$–$C_{16}$ alkanoyloxy group, or a $C_2$–$C_{26}$ dialkylamino group; and the alkyl portion of said groups may be interrupted by:

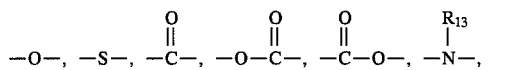

phenylene or phenyleneoxy, wherein $R_{13}$ stands for a hydrogen atom, a lower alkyl, or lower alkanoyl group, or 1 to 3 hydrogen atoms on the carbon atoms of the alkyl portion may be substituted with a phenyl or phenyloxy group, a halogen atom or a cyano group, or the phenyl portion as the substituent may be substituted with a halogen atom, an amino, nitro, cyano, carboxyl or hydroxyl group or a lower alkyl, lower alkoxy, lower monoalkylamino, lower dialkyamino, lower alkanoylamino, lower alkyloxycarbonyl, lower alkanoyl or lower alkanoyloxy group;

$R_2$ stands for a hydrogen atom or a $C_1$–$C_8$ alkyl group;

each $R_3$ independently stands for a hydrogen atom, a halogen atom, an amino, nitro, cyano, carboxyl or hydroxyl group, $C_1$–$C_{20}$ alkyl, $C_1$–$C_{20}$ alkoxy, $C_1$–$C_{20}$ monoalkylamino, $C_1$–$C_{20}$ alkanoylamino, $C_1$–$C_{20}$ alkyloxycarbonyl, $C_1$–$C_{20}$ alkanoyl or $C_1$–$C_{20}$ alkanoyloxy group, or a $C_2$–$C_{20}$ dialkylamino group; and $R_5$, $R_6$, $R_7$, and $R_8$ each independently stands for a hydrogen atom or a $C_1$–$C_{20}$ alkyl group, or $R_5$ and $R_6$ or $R_7$ and $R_8$ combine with a carbon atom bonded thereto to form a $C_5$–$C_7$ carbon ring; and n is 0 or 1.

8. A method according to claim 7, wherein the substituent S stands for a group represented by the formula:

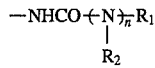

wherein $R_1$, $R_2$ and n are the same as defined in claim 7.

* * * * *